(12) United States Patent
Rasche et al.

(10) Patent No.: US 10,732,244 B2
(45) Date of Patent: Aug. 4, 2020

(54) SYSTEMS, METHODS, APPARATUSES, AND COMPUTER-READABLE STORAGE MEDIA FOR PERFORMING DIAGNOSTIC EXAMINATIONS USING MRI

(75) Inventors: Volker Rasche, Erbach (DE); Erich Hell, Giengen (DE); Johannes Ulrici, Darmstadt (DE)

(73) Assignee: Sirona Dental Systems GMBH, Bensheim (DE)

( * ) Notice: Subject to any disclaimer, the term of this patent is extended or adjusted under 35 U.S.C. 154(b) by 768 days.

(21) Appl. No.: 13/429,928

(22) Filed: Mar. 26, 2012

(65) Prior Publication Data

US 2013/0252196 A1    Sep. 26, 2013

(51) Int. Cl.

| | | |
|---|---|---|
| *G01R 33/54* | (2006.01) | |
| *G01R 33/341* | (2006.01) | |
| *A61B 5/055* | (2006.01) | |
| *A61B 5/00* | (2006.01) | |
| *G01R 33/28* | (2006.01) | |
| *G01R 33/561* | (2006.01) | |

(52) U.S. Cl.
CPC .......... *G01R 33/546* (2013.01); *A61B 5/0033* (2013.01); *G01R 33/341* (2013.01); *A61B 5/0555* (2013.01); *G01R 33/28* (2013.01); *G01R 33/561* (2013.01)

(58) Field of Classification Search
CPC ............ G01R 33/54–546; G01R 33/34; G01R 33/341–3415; A61B 5/0033; A61B 5/0037; A61B 5/004; A61B 5/005–0555

USPC .... 600/410, 411, 407, 417, 429; 378/17, 37; 424/58; 606/130; 324/310; 382/131, 382/218, 132

See application file for complete search history.

(56) References Cited

U.S. PATENT DOCUMENTS

| | | |
|---|---|---|
| 5,085,219 A | 2/1992 | Ortendahl et al. ......... 128/653.5 |
| 5,498,961 A | 3/1996 | Kuhn et al. |
| 5,501,218 A * | 3/1996 | Usui ............................ 600/410 |
| 5,502,385 A | 3/1996 | Kuhn et al. |
| 5,644,234 A | 7/1997 | Rasche et al. |
| 5,677,627 A | 10/1997 | Rasche |
| 5,823,959 A | 10/1998 | Rasche |
| 5,933,006 A | 8/1999 | Rasche et al. |
| 5,938,599 A | 8/1999 | Rasche et al. |
| 5,969,525 A | 10/1999 | Van Driel et al. |

(Continued)

FOREIGN PATENT DOCUMENTS

| | | |
|---|---|---|
| CA | 2 766 453 A1 | 12/2010 |
| CN | 101347330 A | 1/2009 |

(Continued)

OTHER PUBLICATIONS

Boeddinghaus, Current concepts in maxillofacial imaging, European Journal of Radiology 66 (2008) 396-418.*

(Continued)

*Primary Examiner* — Angela M Hoffa
(74) *Attorney, Agent, or Firm* — Venable LLP

(57) ABSTRACT

A method for operating an imaging system, and a system, apparatus, and computer-readable medium, that operate in accordance with the method. The method includes providing field-of-view (FoV) information, and automatically selecting at least one recording sequence based on at least one of a particular diagnostic application of interest and the FoV information.

66 Claims, 10 Drawing Sheets

(56) References Cited

U.S. PATENT DOCUMENTS

| | | | | |
|---|---|---|---|---|
| 6,118,842 A * | 9/2000 | Arai | A61B 6/032 | 378/38 |
| 6,195,409 B1 * | 2/2001 | Chang | A61B 5/055 | 378/20 |
| 6,236,205 B1 | 5/2001 | Ludeke et al. | | |
| 6,397,094 B1 | 5/2002 | Ludeke et al. | | |
| 6,411,088 B1 | 6/2002 | Kuth et al. | | |
| 6,603,494 B1 * | 8/2003 | Banks | A61B 5/055 | 600/410 |
| 6,736,776 B2 * | 5/2004 | Miles | G06Q 10/10 | 128/920 |
| 6,778,849 B1 * | 8/2004 | Ninomiya | A61B 5/055 | 324/318 |
| 7,612,562 B2 * | 11/2009 | Yasuhara | G01R 33/307 | 324/318 |
| 7,646,199 B2 * | 1/2010 | Dannels | G01R 33/34007 | 324/307 |
| 8,212,558 B2 * | 7/2012 | Mueller | A61B 5/055 | 324/307 |
| 8,587,312 B2 * | 11/2013 | Biber | G01R 33/3415 | 324/318 |
| 8,744,162 B2 * | 6/2014 | Greenwood | G06T 7/0012 | 378/38 |
| 8,847,597 B2 | 9/2014 | Rasche et al. | | |
| 9,000,767 B2 * | 4/2015 | Schmidt | G01R 33/34084 | 324/318 |
| 9,226,685 B2 * | 1/2016 | Choe | A61B 5/0555 | |
| 9,618,598 B2 * | 4/2017 | Grodzki | G01R 33/341 | |
| 9,684,045 B2 * | 6/2017 | Marzendorfer | G01R 33/445 | |
| 2002/0016600 A1 * | 2/2002 | Cosman | 606/130 | |
| 2003/0235265 A1 * | 12/2003 | Clinthorne et al. | 378/4 | |
| 2004/0147840 A1 * | 7/2004 | Duggirala | A61B 8/00 | 600/437 |
| 2005/0020902 A1 * | 1/2005 | Janes | A61B 6/032 | 600/407 |
| 2006/0273790 A1 * | 12/2006 | Eggers et al. | 324/309 | |
| 2007/0053486 A1 * | 3/2007 | Zelnik | A61B 6/04 | 378/20 |
| 2007/0096739 A1 * | 5/2007 | Nakabayashi | G01R 33/3415 | 324/318 |
| 2007/0109294 A1 * | 5/2007 | Gotman | A61B 6/00 | 345/418 |
| 2007/0188171 A1 * | 8/2007 | Garwood et al. | 324/310 | |
| 2009/0048505 A1 | 2/2009 | Kuth et al. | | |
| 2009/0093706 A1 | 4/2009 | Zhang et al. | | |
| 2009/0264733 A1 * | 10/2009 | Corum | A61B 5/055 | 600/420 |
| 2009/0310846 A1 * | 12/2009 | Lemchen | G06T 19/003 | 382/132 |
| 2010/0054556 A1 * | 3/2010 | Novatzky | G06F 19/321 | 382/128 |
| 2010/0076301 A1 * | 3/2010 | Elgort et al. | 600/411 | |
| 2010/0201360 A1 * | 8/2010 | Morita | A61B 5/0555 | 324/309 |
| 2011/0046475 A1 * | 2/2011 | Assif | G01R 33/24 | 600/422 |
| 2011/0082361 A1 * | 4/2011 | Jattke | A61B 5/055 | 600/410 |
| 2011/0103668 A1 * | 5/2011 | Uchizono | G01R 33/561 | 382/131 |
| 2011/0113376 A1 | 5/2011 | Suzuki et al. | | |
| 2011/0305320 A1 * | 12/2011 | Suuronen | A61B 6/00 | 378/98.5 |
| 2012/0093384 A1 * | 4/2012 | Goto | G01R 33/56509 | 382/131 |
| 2012/0223711 A1 * | 9/2012 | Weinberg | G01R 33/3852 | 324/309 |
| 2012/0288820 A1 * | 11/2012 | Choe | A61B 5/0555 | 433/29 |
| 2013/0165767 A1 * | 6/2013 | Darrow | G01R 33/543 | 600/414 |
| 2013/0190608 A1 * | 7/2013 | Schmidt | A61B 5/055 | 600/422 |
| 2013/0218000 A1 * | 8/2013 | Coppens | A61B 5/004 | 600/411 |
| 2014/0148686 A1 * | 5/2014 | Thevathasan | A61B 5/6835 | 600/415 |

FOREIGN PATENT DOCUMENTS

| | | |
|---|---|---|
| CN | 102058409 A | 5/2011 |
| WO | 2010/149686 A1 | 12/2010 |

OTHER PUBLICATIONS

Bracher, A. K. et al., *Feasibility of Ultra-Short Echo Time (UTE) Magnetic Resonance Imaging for Identification of Carious Lesions*, Magnetic Resonance in Medicine, vol. 66, pp. 538-541 (2011).

International Search Report issued by the European Patent Office in connection with International Application No. PCT/EP2013/05633, dated Jul. 30, 2013.

Office Action issued in Chinese Patent Application No. 201380016749.9, dated Mar. 11, 2016.

* cited by examiner

SYSTEMS, METHODS, APPARATUSES, AND COMPUTER-READABLE STORAGE MEDIA FOR PERFORMING DIAGNOSTIC EXAMINATIONS USING MRI

BACKGROUND

Field

The present disclosure relates to diagnostic examinations performed using Magnetic Resonance Imaging (MRI), and more particularly to systems, methods, apparatuses, and computer-readable storage media for performing dental examinations using MRI.

Description of Related Art

Performing diagnostic examinations using conventional MRI systems can be time consuming and complex. Accordingly, highly-skilled technicians can be required to perform such examinations. Before a diagnostic inquiry is performed and a corresponding diagnostic image is recorded in modern clinical practice, a conventional MRI system used to acquire the diagnostic image can require meticulous preparation in order to achieve localization of a target volume and to obtain an optimal image quality, which depends on the particular diagnostic inquiry being performed.

FIG. 8 shows a flow chart 700 of a procedure that can be performed when a conventional MRI system is used to perform a diagnostic examination. The procedure begins in Step S802.

In Step S804, one or more imaging coils are positioned near an area of the patient's body that is to be examined. The imaging coils can be High Frequency (HF) coils, for example, that are integrated within the MRI system or that are not integrated within the MRI system. Imaging coils integrated within the MRI system can be used for general investigations, for example, investigations of a large area of the patient's body. For an investigation of a particular body part, imaging coils external to the MRI system can be positioned near the body part. For example, if the patient's carotid artery is being investigated, the technician might be required to place an external HF coil adjacent the patient's carotid artery.

In Step S806, at least part of a patient's body is positioned in the MRI system.

In Step S808, the technician defines one or more recording sequences suitable for a particular diagnostic inquiry. Excitation and measurement signals transmitted and received by the HF and gradient coils during each MRI scan are based on parameters included in each recording sequence. Each recording sequence can include a plurality of parameters that can be changed by the technician via a user interface, which can be time consuming.

Multiple recording sequences can be used to obtain multiple properties of an object at various resolutions and degrees of contrast. Multiple recording sequences can be used to address differing requirements of different diagnostic inquiries.

In Step S810, a scout recording is obtained. The scout recording can be a general image of an entire object. The scout image can be used to check whether the patient is positioned properly with respect to the imaging coil. The scout image need not have an image quality that is sufficient for making a diagnosis. The scout recording can be required for defining the final region of interest during subsequent scans, which can be quite time consuming In Step S812, a sensitivity profile of the imaging coil is generated based on a plurality of measurements. The sensitivity profile of the coil depends on the location of the coil within the magnet. If the location is fixed, the sensitivity profile remains the same. The sensitivity profile can be used to correct subsequently obtained diagnostic images. The sensitivity profile can be used in conjunction with parallel imaging techniques. If parallel imaging techniques are not used, the sensitivity profile of the imaging coil need not be generated.

In Step S814, a target volume is defined within a scout volume or three-dimensional region corresponding to the scout image obtained in Step S810. The target volume defines a three-dimensional region in which a diagnostic scan is to be performed to obtain a recording of a diagnostic image. An image quality of the diagnostic image is often greater than the image quality of the scout image.

It is noted that the sensitivity profile of the receive coil does need not necessarily be measured in a separate step before each image acquisition. If a scout image is taken, the scout image is a convolution of an MR signal of the object with a sensitivity profile of the receive coil. Measurement of the sensitivity profile of the receive coil can be integrated into the scout scan or even directly into an imaging sequence. For the latter method, no separate calibration step is needed. Generally, coil calibration procedures do not require user interaction.

In Step S816, one or more diagnostic images are recorded based on the imaging sequence(s) defined in Step S808. The process ends in Step S818.

In general, a highly-skilled technician is required to perform Step S804. Such a highly-skilled technician should have great expertise and precise knowledge of a target organ that is to be examined, in order to ensure that the imaging coil is optimally positioned relative to the area being examined. A highly-skilled technician also can be required to perform Step S808, as the technician should understand a correlation between a particular recording sequence and a particular MRI application, such as a dental MRI application, for example. Additionally, performing Step S808 can include entering parameters that define the recording sequence via a user interface, which can be time consuming. Thus, the amount of time needed to perform an examination that includes Steps S810 to S814 often can be long compared to examinations that do not require a scout image to be obtained.

Accordingly, it would be useful to provide an imaging system that enables an operator to quickly perform a diagnostic examination, without requiring the operator to spend time generating a recording sequence that is used by the imaging system to perform the diagnostic examination or for manual, interactive target volume definition. Additionally, it would be useful to provide an imaging system that can be operated by technicians who are not necessarily highly trained and/or skilled.

SUMMARY

The foregoing and other limitations are overcome by a method for operating an imaging system, and by a system, apparatus, and computer-readable medium that operate in accordance with the method.

In accordance with one example aspect herein, the imaging system is a magnetic resonance imaging (MRI) system, and the method includes providing field-of-view (FoV) information, and automatically selecting at least one recording sequence based on at least one of a particular diagnostic application of interest and the FoV information.

The FoV information can be provided based on a region of interest (ROI). Additionally, the FoV information can be provided based on at least one of a position of the ROI, and a size of the ROI. In one example, at least one of the position and size of the ROI correspond with the particular diagnostic application of interest, and the method further includes selecting the particular diagnostic application of interest. A region of interest can be displayed in response to the selecting of the particular diagnostic application of interest.

The method can include obtaining information indicative of a region occupied by an imaging coil positioned near a patient's anatomical structure of interest.

In one example embodiment, the recording sequence includes one or more of at least one HF pulse value, at least one gradient pulse value, at least one time interval between pulses, at least one waveform amplitude, at least one waveform shape, at least one waveform length, and at least one timing value for measuring and/or reading out HF signals. The recording sequence can be generated based on at least one of a position of an anatomical structure of interest, a field of view, the particular diagnostic application of interest, at least one characteristic of the anatomical structure of interest, and at least one predetermined image resolution. The recording sequence also can be generated based on patient-specific information (e.g. an amount of metal fillings).

Also in one example embodiment, the method includes performing at least one scan of an object of interest, based on at least one parameter included in the at least one recording sequence.

The method also can include providing at least one diagnostic image based on the at least one recording sequence.

The method can enable diagnostic examinations to be performed by technicians who are not necessarily trained to generate recording sequences or to define target volumes for diagnostic image acquisition from scout images.

DETAILED DESCRIPTION

Figure 1A:
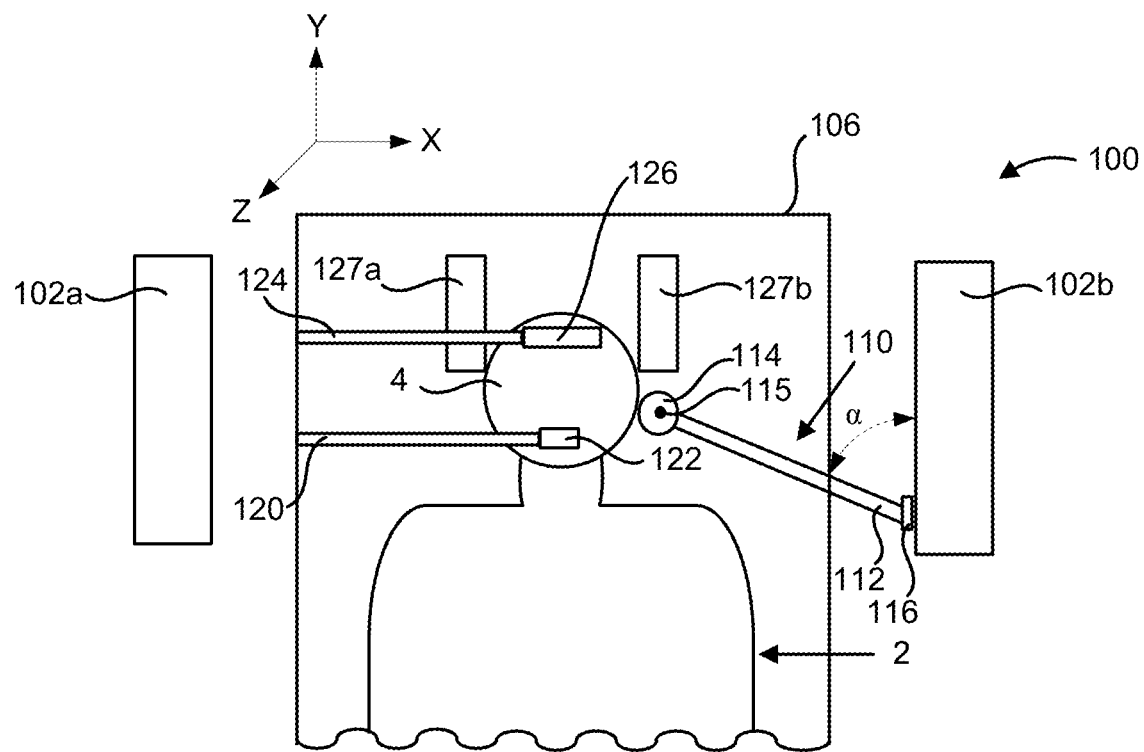
FIG. 1A illustrates a dental MRI system according to an example embodiment herein, and a patient.

FIG. 1A illustrates a dental MRI system 100 according to an example embodiment herein. The dental MRI system 100 includes a first housing portion 102a and a second housing portion 102b in which a main magnet (not illustrated) and gradient coils (not illustrated) are disposed. The main magnet can include two opposing poles or have a toroidal shape, for example. For illustrative purposes, only the first and second housing portions 102a and 102b are shown in FIG. 1A, however, the complete housing (not shown) can have a toroidal shape.

The dental MRI system 100 also includes a supporting platform 106 (e.g. a chair or a bed) that supports a patient 2. Additionally, the dental MRI system 100 includes a patient fixture in the form of a head rest assembly 126, which includes, for example, head holders 127a and 127b between which a head 4 of the patient 2 can be placed to hold the head 4 of the patient 2 in a fixed or predetermined position. The head rest assembly 126 can be attached to the supporting platform 106, for example, by attaching the head rest assembly 126 to the head rest arm 124 and attaching the head rest arm 124 to the patient support 106.

An HF coil assembly 110 can be attached to the second housing portion 102b, the supporting platform 106, or the head rest assembly 126. In the illustrated example, the HF coil assembly 110 includes a coil arm 112, an imaging or HF coil 114 that includes an indicator 115 (e.g., a Light Emitting Diode (LED), and a measuring device 116. Also, in one example the coil arm 112 is pivotally attached to the second housing portion 102b using a ball and socket joint (not illustrated), or other suitable pivot mechanism, so that the coil arm 112 can be moved to position the HF coil 114 near a particular portion (e.g., the mouth) of the patient 2. The measuring device 116 includes angular position measuring devices that measure angles α and β formed by the coil arm 112 relative to the second housing portion 102b, for example. The angular position measuring devices can include circular potentiometers having resistances that are proportional to the angles being measured. The measuring device 116 can output signals indicating values of the angles α and β formed by the coil arm 112 relative to the second housing portion 102b. Those signals are digital signals, in one example embodiment, although in other embodiments they can be analog, and can be converted to digital form by an A/D converter. Additionally, the length of the coil arm 112 can be adjustable and a conventional measuring device can determine the actual length of the coil arm 112 after the HF coil 114 is moved to a desired position.

The portion of the patient's body to be imaged must be positioned within a field of view (FoV) of the dental MRI system 100. In one example, the FoV is determined by at least the following three factors. A first factor includes a location of a fixed or predetermined area/volume in which the magnetic field of the main magnet is homogeneous, which is determined by physical properties of the main magnet. A second factor includes characteristics of the magnetic fields produced by the gradient coils, which are determined by an imaging or recording sequence. A third factor includes characteristics of a sensitive area of the HF coil 114, which are determined by physical properties and the position or location of the HF coil 114.

A region of interest (ROI) is a portion within the patient 2 that is to be imaged. The position of the ROI and a position of a part of the patient to be scanned can be identical, but need not be. In order for measurements to be taken from within the ROI, the ROI should lie within the FoV of the dental MRI system 100. Accordingly, a position or location of the ROI with respect to the magnetic field of the main magnet are known or determined. In one example, the position or location of the ROI with respect to the magnetic field of the main magnet can be determined by fixing the patient 2 such that the ROI is in a known position with respect to the magnetic field of the main magnet. This can be accomplished by using a patient fixture in the form of a bite plate 122 secured in the patient's mount 2 to fix the position and/or location with respect to the main magnet, or by positioning the patient's head 4 such that the patient's front teeth are in the center of cross lines produced by a laser unit (not shown), which is in a fixed or predetermined position or location with respect to the main magnet.

The position or location of the ROI with respect to the magnetic field of the main magnet can be measured by a dedicated measurement device (e.g., digital camera unit 250). Alternatively, the bite plate 122 can be movable and its position can be determined using a dedicated measurement device (not shown) integrated into the bite plate arm 120, for example. Alternatively, cross lines produced by the laser unit can be positioned such that the cross lines are centered on the patient's front teeth and the position of the laser unit is measured.

An example embodiment includes RF micro coils that return RF signals when excited by external RF fields. The RF micro coils can be seen in an MRI image as bright spots. The RF micro coils can be floating coils that are positioned at the ROI to act as MRI markers indicating the position of the ROI.

Additionally, the position of the ROI can be determined by performing a pre-scan operation. Because performing the pre-scan operation can be time consuming, in one example the dental MRI system 100 does not determine the position of the ROI by performing pre-scans.

The position of the HF coil 114 can be used to determine the position of the ROI, if the HF coil 114 is positioned on or at a particular anatomical structure. The position of the HF coil 114 yields the position of the anatomical structure (as will be described below) and, thus, the position of the ROI. Accordingly, the position of the anatomical structure need not be determined by additional position detection means.

Figure 2A:
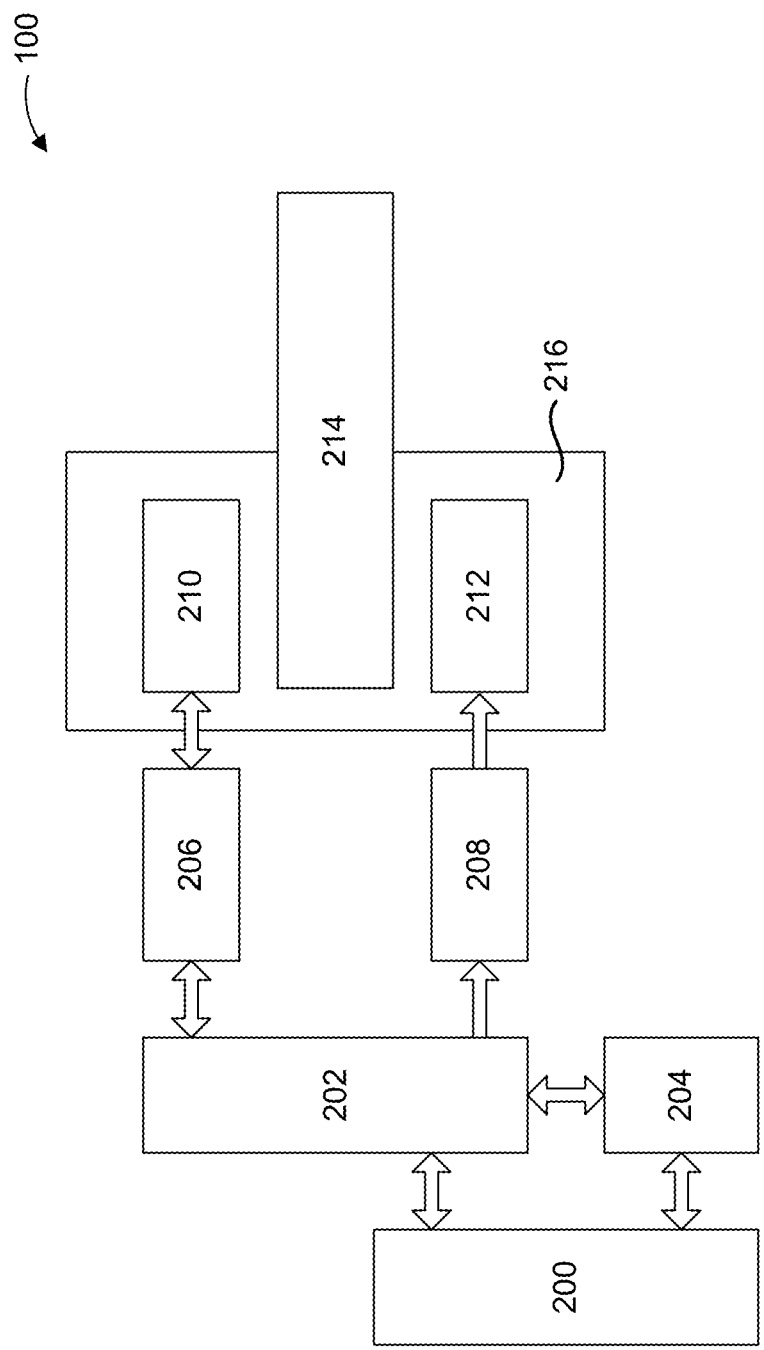
FIG. 2A illustrates a functional diagram of the dental MRI system shown in FIG. 1A.

FIG. 2A illustrates a functional diagram of the dental MRI system 100. The dental MRI system 100 of this illustration includes a user interface unit 200, a spectrometer or sequencer unit 202, an image reconstruction unit 204, an HF signal amplification unit 206, a gradient signal amplification unit 208, an HF coil unit 210 that includes at least one transmit HF coil and at least one receive HF coil, a gradient coil unit 212 that includes at least three gradient coils for x, y, and z coordinate encoding, respectively, an area 214 in which the patient 2 can be positioned, and a main magnet 216. In an embodiment, the transmit HF coil and the receive HF coil are the same coil. The gradient coil unit 212, transmit HF coil, and the receive HF coil can be located within the main magnet 216 and each coil can include two opposing poles. The main magnet 216 has a magnetic field that is fixed and, thus, the magnetic field of the main magnet 216 does not change during an imaging sequence.

Figure 2B:
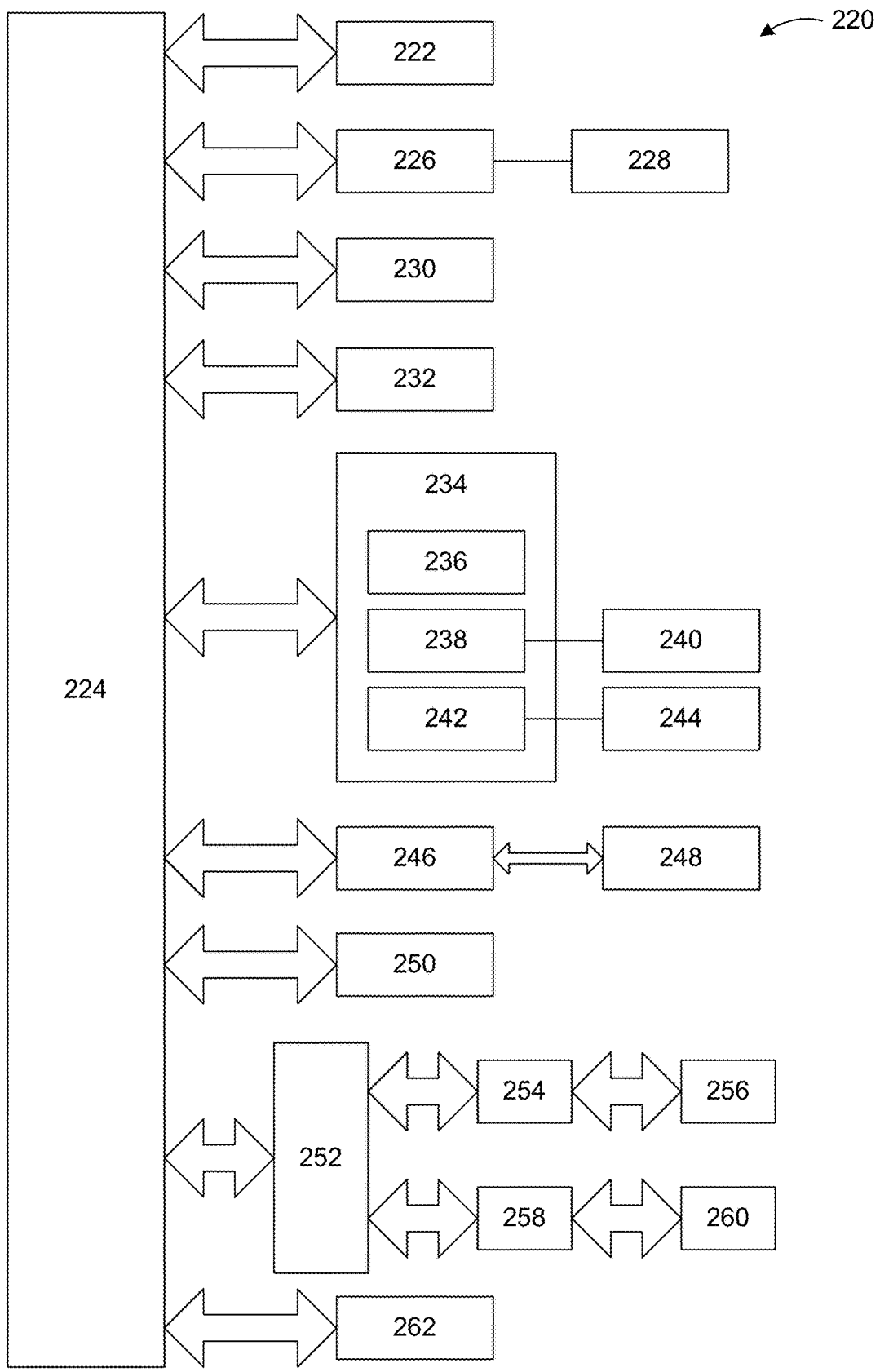
FIG. 2B illustrates a system architecture of a portion of the MRI system shown in FIG. 1A.

The user interface unit 200 can be used to select a predefined recording sequence that is stored in a memory device (e.g., the secondary memory 234 shown in FIG. 2B). The user interface unit 200 also can be used to control displaying of images, which a medical professional can operate to help make a medical diagnosis.

Figure 7:
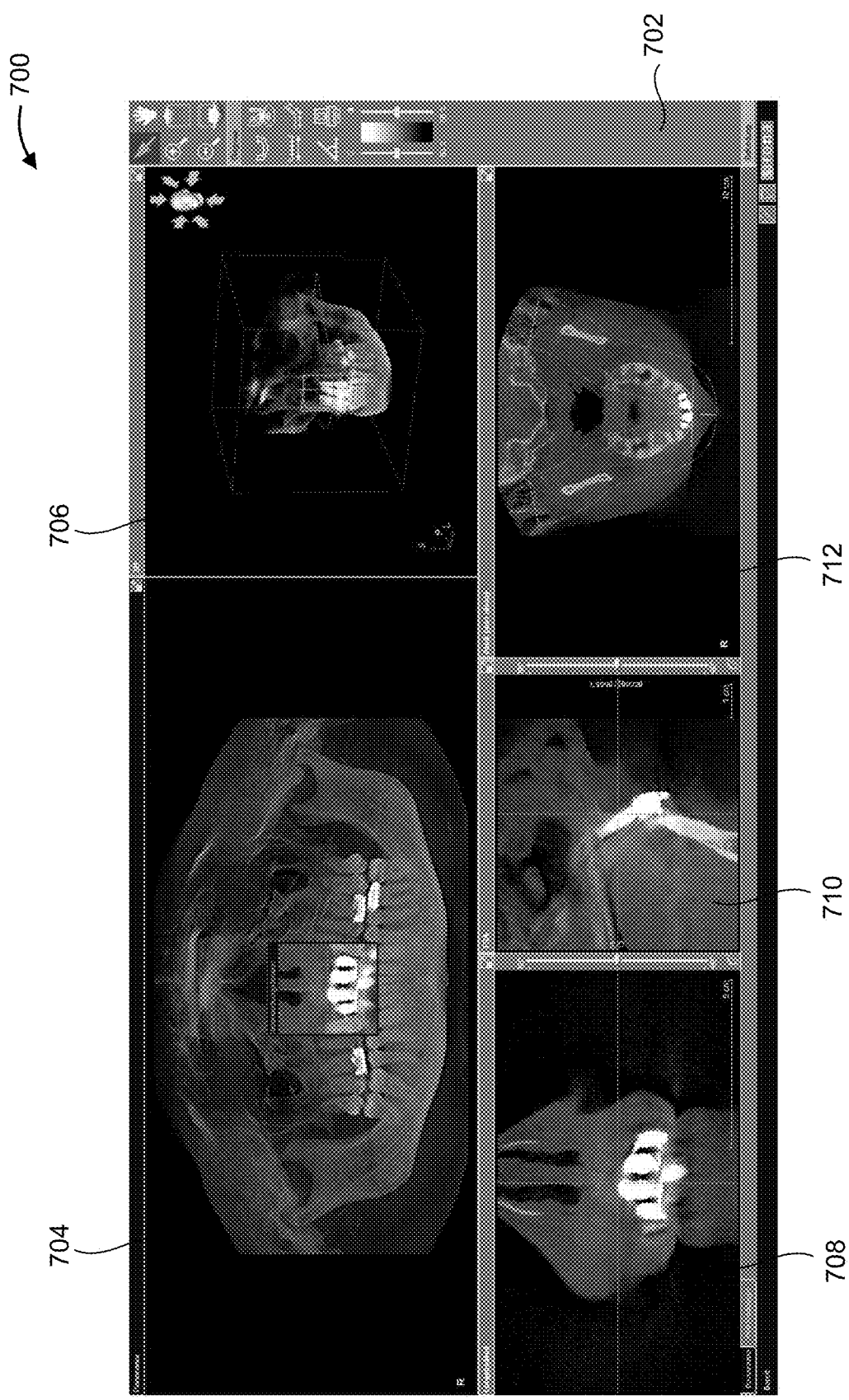
FIG. 7 shows examples of diagnostic images generated by computed tomography (CT) scans that can be displayed by the dental MRI system shown in FIG. 1A.
Figure 8:
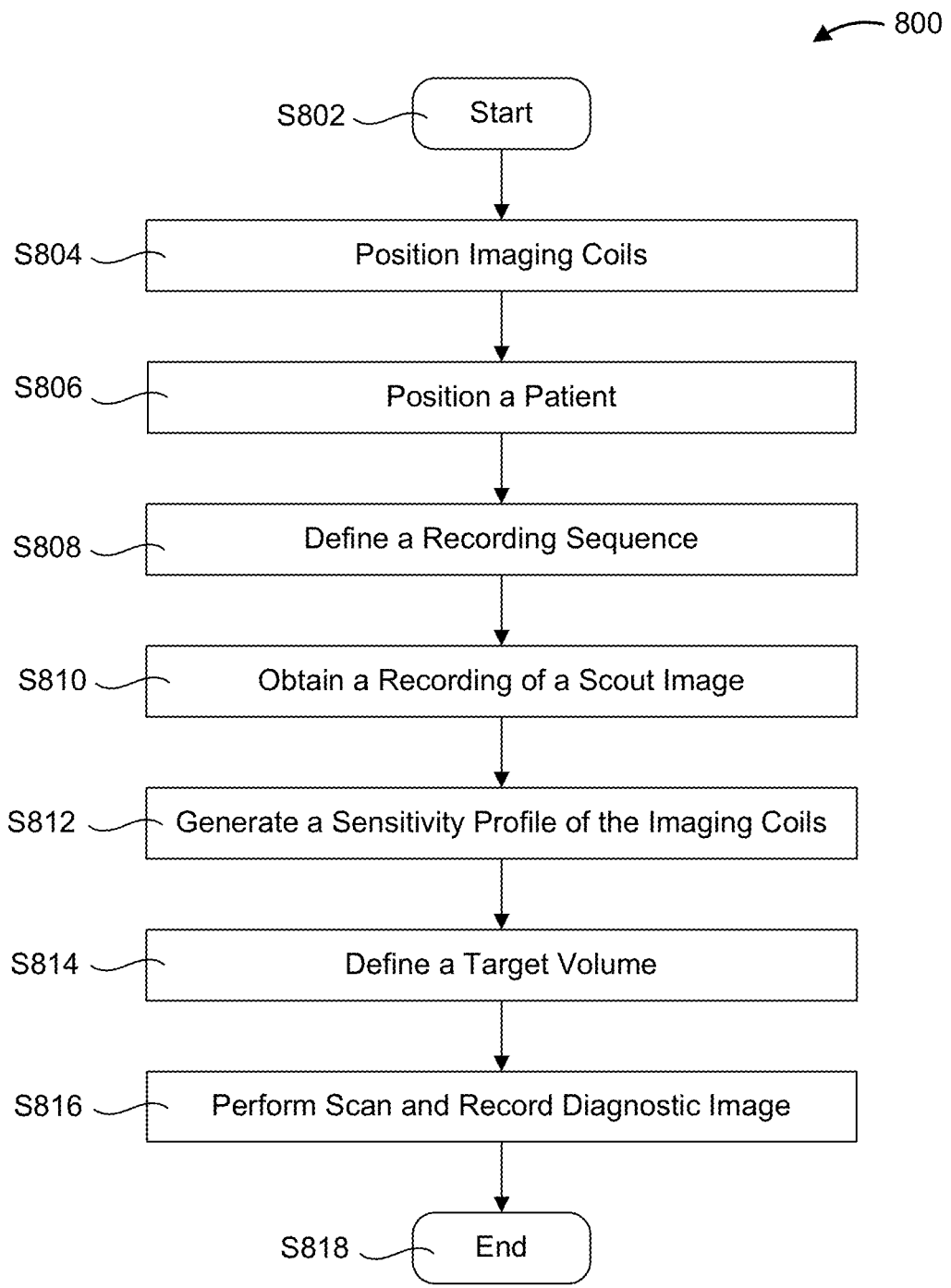
FIG. 8 is a flow chart of a process for performing a diagnostic examination using a conventional MRI system.

FIG. 7 shows several slice views common for dental computed tomography (CT) scans that can be displayed by the dental MRI system 100. For example, the display area 700 can be displayed by the display unit 228 (or other output unit). The display area 700 includes a control area 702 that a user can manipulate to change display properties. The display area 700 includes a panoramic view 704, a volumetric view 706, a longitudinal (i.e. tangential to maxillary crest) view 708, a transversal (i.e. perpendicular to maxillary crest) view 710, and an axial view (from above, slice parallel to plane of maxillary crest) 712. Each of the two-dimensional slices shown in FIG. 7 can have a predefined orientation with respect to an anatomical structure. In one example, the processor 222 can cause the display unit 228 to display a slice in a plane generated by one or more dental roots, or in a plane generated by a transmandibular joint of a patient.

For example, when the processor 222 causes the display unit 228 to display a slice in a plane generated by one dental root, a center line of the dental root is determined and the plane is chosen such that it runs orthogonal (or tangential) to the maxillary crest, and runs through the central line of the dental root. When the processor 222 causes the display unit 228 to display a slice in a plane generated by two dental roots, the plane generated by the two dental roots is determined by determining central lines of both dental roots and spanning a plane between them, for example. When the processor 222 causes the display unit 228 to display a slice in a plane generated by three dental roots, three different planes can be generated resulting in three different views, for example.

The sequencer unit 202 provides control signals to the HF signal amplification unit 206 and the gradient signal amplification unit 208. The control signals can be used for switching or changing characteristics of electromagnetic fields produced by the HF coil unit 210 and/or the gradient coil unit 212, as well as for steering signal readout. The sequencer unit 202 also provides timing values for correct switching of Gradient and HF signals, both of which are coordinated in a predefined manner. The control signals provided to the gradient signal amplification unit 208 by the sequencer unit 202 can include, for example, data specifying a size of a desired magnetic field strength of the gradient coils 208 and a desired rise time of the magnetic field of the gradient coils 208.

The control signals provided to the HF signal amplification unit 206 by the sequencer unit 202 can include, for example, data indicating a duration and a strength of an HF transmit pulse to be transmitted by the HF coil unit 210, and a frequency and a shape of the HF transmit pulse. The control signals provided to the HF signal amplification unit 206 by the sequencer unit 202 can set parameters used for data acquisition. For example, the control signals can include parameters indicating a measurement value, an analog-to-digital conversion value of a desired signal level, a value used for data buffering, and one or more readout timing values. The sequencer unit 202 also is responsible for setting timing values of the recording sequences.

The gradient signal amplification unit 208 and the gradient coil unit 212 operate in conjunction to superimpose a three-dimensional magnetic field gradient in x, y, and z directions onto the magnetic field produced by the main magnet 216. The sequencer unit 202 provides the gradient signal amplification unit 208 with control signals that include parameter values indicating a size or a magnitude of a desired gradient field strength, a duration of applied gradient pulses, and one or more change rates of gradient fields that are varied during a recording sequence. The gradient signal amplification unit 208 causes the gradient coil unit 212 to produce magnetic fields based on the parameter values provided by the sequencer 202.

The HF signal amplification unit 206 and HF coil unit 210 operate in conjunction to transmit, receive, and measure radio frequency signals or HF signals. The sequencer unit 202 provides the HF signal amplification unit 206 with control signals that include parameter values indicating a pulse width, a pulse shape, a pule duration, and a pulse frequency used in a recording sequence. The recording sequence parameters provided by the sequencer unit 202 to the HF signal amplification unit 206 are used to cause the HF signals produced by the HF coil unit 210 to vary in such a way that data used to form a particular type of diagnostic image is obtained.

In general, in an MRI sequence, elementary spins within an object are excited by an HF pulse. When returning to an equilibrium state, the spins emit HF radiation again, which is measured. Non-limiting examples of types of recording sequences include a spin-echo-sequence type, a gradient-echo-sequence type, an ultra-short-echo-time type, zero-echo-time type, and a SWIFT type, which are well known to one of ordinary skill in the art. A spin-echo-sequence type of recording sequence can show little sensitivity to magnetic field distortions that can increase acquisition times. A gradient-echo-sequence type of recording sequence can provide a shorter acquisition time, but can be subject to more magnetic field distortions and can show a lower image contrast. An ultra-short-echo-time type, a zero-echo-time type, and a SWIFT type of recording sequence can measure a signal shortly after or even during excitation, such that signal decay is very low.

The HF signals received by the HF signal amplification unit 206 from the HF coil unit 210 are measured, digitized, and provided to the image reconstruction unit 204 (by way of the sequencer unit 202). The image reconstruction unit 204 can improve image quality by performing noise filtering processing on the received HF signals. Additionally, the image reconstruction unit 204 can highlight particular features in an image, for example, by inverting the colors in the image. For example, if the original image is a black and white image, the image reconstruction unit 204 can cause black portions in the original image to be displayed as white portions, and can cause white portions in the original image to be displayed as black portions. Alternatively, diagnostically interesting regions can be highlighted with different colors.

In one exemplary embodiment, the dental MRI system 100 also includes at least one computer system 220, as shown in FIG. 2B. The computer system 220 includes at least one computer processor 222 (e.g. a central processing unit or a multiple processing unit). The processor 222 is connected to a communication infrastructure 224 (e.g., a communications bus, a cross-over bar device, or a network). Although various embodiments are described herein in terms of this exemplary computer system 220, after reading this description, it will become apparent to a person skilled in the relevant art(s) how to implement the invention using other computer systems and/or architectures.

The computer system 220 also includes a display interface (or other output interface) 226 that forwards video graphics, text, and other data from the communication infrastructure 224 (or from a frame buffer (not shown)) for display on a display unit 228 (or other output unit). The processor 222 can cause the display unit 228 to display one or more of the two-dimensional slice views shown in FIG. 7 based on a type of dento-maxillofacial diagnostic application that is selected. For example, based on a check mark that has been placed in the first portion 302 of the user interface screen 300 shown in FIG. 3 to select an application, the processor 222 can cause the display unit 228 to display a predetermined one or more of the two-dimensional slice views shown in FIG. 7.

The computer system 220 also includes an input unit 230 that can be used by a user of the computer system 220 to send information to the computer processor 222. For example, the input unit 230 can include a keyboard device and/or a mouse device or other input device. In one example, the display unit 228, the input unit 230, and the computer processor 222 can collectively form the user interface unit 200 shown in FIG. 2A (or only elements 228 and 230 form unit 200).

In an example embodiment that includes a touch screen, for example, the input unit 230 and the display unit 228 can be combined. In such an embodiment, an operator touching the display unit 228 can cause corresponding signals to be sent from the display unit 228 to the display interface 226, which can forward those signals to a processor such as processor 222, for example.

In addition, the computer system 220 includes a main memory 232, which preferably is a random access memory ("RAM"), and also can include a secondary memory 234. The secondary memory 234 can include, for example, a hard disk drive 236 and/or a removable-storage drive 238 (e.g., a floppy disk drive, a magnetic tape drive, an optical disk drive, a flash memory drive, and the like). The removable-storage drive 238 reads from and/or writes to a removable storage unit 240 in a well-known manner. The removable storage unit 240 can be, for example, a floppy disk, a magnetic tape, an optical disk, a flash memory device, and the like, which is written to and read from by the removable-storage drive 238. The removable storage unit 240 can include a computer-usable storage medium having computer software instructions and/or data stored therein.

In alternative embodiments, the secondary memory 234 can include other computer-readable media storing computer-executable programs or other instructions to be loaded into the computer system 220. Such devices can include a removable storage unit 244 and an interface 242 (e.g., a program cartridge and a cartridge interface similar to those used with video game systems); a removable memory chip (e.g., an erasable programmable read-only memory ("EPROM") or a programmable read-only memory ("PROM")) and an associated memory socket; and other removable storage units 244 and interfaces 242 that allow software and data to be transferred from the removable storage unit 244 to other parts of the computer system 220.

The computer system 220 also can include a communications interface 246 that enables software and data to be transferred between the computer system 220 and external devices (not shown). Examples of the communications interface 246 include a modem, a network interface (e.g., an Ethernet card), a communications port (e.g., a Universal Serial Bus ("USB") port or a FireWire® port), a Personal Computer Memory Card International Association ("PCMCIA") interface, and the like. Software and data transferred via the communications interface 246 are in the form of signals, which can be electronic, electromagnetic, optical or another type of signal that is capable of being transmitted and/or received by the communications interface 246. Signals are provided to the communications interface 246 via a communications path 248 (e.g., a channel). The communications path 248 caries signals and can be implemented using wire or cable, fiber optics, a telephone line, a cellular link, a radio-frequency ("RF") link, or the like.

The computer system 220 also can include a digital camera unit 250 that generates data representing images captured by the digital camera unit 250. The data generated by the digital camera unit 250 can be processed by the processor 222 and/or stored in the secondary memory 234. For example, the processor 222 can process the data generated by the digital camera unit 250 to precisely determine a location of an object imaged by the digital camera unit 250. The digital camera unit 250 can include a USB interface for connecting the digital camera unit 250 to the communications infrastructure 224, for example. The digital camera unit 250 also can include a wireless interface (e.g., an IEEE 802.11 wireless Local Area Network (LAN) interface or a Bluetooth interface) for connecting the digital camera unit 250 to the communications infrastructure 224.

The computer system 220 also can include a spectrometer or sequencer unit 252, an image reconstruction unit 204, a gradient signal amplification unit 254, a first transmitting unit 256, an HF signal amplification unit 258, and a second transmitting unit 260. The sequencer unit 252 provides control signals to the gradient signal amplification unit 254 and the HF signal amplification unit 258.

The computer system 220 can also include a measurement device 262 that measures physiological signals, which can be incorporated in the MRI device. Such physiological signals can be, for example and without limitation, electrocardiography (ECG) signals or signals indicating the movement of the temporomandibular joint (TMJ).

Additionally, the computer system 220 can include a measuring unit 256. The measuring unit 256 can include, for example, a plurality of sensors and can be operated to function as the measuring device 116. The measuring unit 256 can be connected to the communications infrastructure 224 via an USB interface, for example. Signals output by the measuring unit 256 can be stored, for example, in a memory, such as main memory 232 (FIG. 2B).

One or more computer programs (also referred to as computer control logic) are stored in the main memory 232 and/or the secondary memory 234. The computer programs also can be received via the communications interface 246. The computer programs include computer-executable instructions which, when executed by the computer processor 222, cause the computer system 220 to perform the procedures as described herein and shown in FIG. 4, for example. Accordingly, the computer programs can control the overall computer system 220.

In one example embodiment herein, the software can be stored in a non-transitory computer-readable storage medium and loaded into the computer system 220 using the removable-storage drive 238, the hard disk drive 236, and/or the communications interface 246. Control logic (software), when executed by the processor 222, causes the computer system 220 to perform the procedures described herein.

In another example embodiment hardware components such as application-specific integrated circuits ("ASICs") can be used to carry out the functionality described herein. Implementation of such a hardware arrangement so as to perform the functions described herein will be apparent to persons skilled in the relevant art(s) in view of this description.

Having described the computer system 220 of FIG. 2B, the dental MRI system 100 will now be further described in conjunction with FIG. 2B.

Figure 1B:
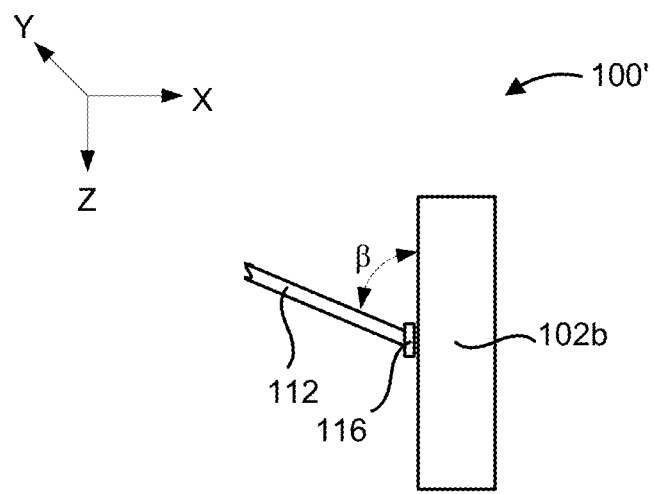
FIG. 1B illustrates part of the dental MRI system shown in FIG. 1A, as viewed from a perspective looking down towards the dental MRI system.

Information indicating dimensions (i.e., length, height, and width) of the coil arm 112 and the HF coil 114 can be predetermined and stored, for example, in a memory, such as the secondary memory 234 (FIG. 2B) or in a memory unit included in the sequencing unit 252. Additionally, information indicating technical characteristics, dimensions, and a three-dimensional position of the main magnet 216 and/or gradient coil unit 208 is stored, for example, in the same memory. The computer processor 222 uses the foregoing information relating to the main magnet 216 and/or the gradient coil unit 208, the coil arm 112, and the imaging coil 114, as well as information indicating values of the angles α and β shown in FIGS. 1A and 1B, respectively, which are measured by measuring device 116, to generate information indicating a three-dimensional location of the imaging coil 114 with respect to a predetermined location of the dental MRI system 100.

The value representing the length of the coil arm 112 and the values of the angles α and β can be used as a three-dimensional polar coordinate. For example, the computer processor 222 can receive the information indicating the values of the length of the coil arm 112 and the angles α and β from the measuring device 116 via the communication infrastructure 224 and use this information to determine a position of the imaging coil 114 with respect to a position of the base of the coil arm 112 (e.g., where a longitudinal axis of the coil arm 112 intersects the left-side surface of the second housing portion 102b). The computer processor 222 can then use information indicating the position of the base of the coil arm 112 relative to a predetermined location of the dental MRI system 100 to determine a position of the HF coil 114 with respect to the predetermined location of the dental MRI system 100.

In one embodiment, the coil arm 112 has a predetermined or fixed length and information indicating the length of the coil arm 112 is stored in the secondary memory 234, for example. In another embodiment, the coil arm 112 includes a telescoping arm that has a variable length. A sensor (not shown) measures a then-current length of the coil arm 112 after the HF coil 114 is positioned near the patient 2 and corresponding information representing the current length of the coil arm 112 at that time is stored in the main memory 232, for example. Additionally, micro coil tracking can be employed, as described above The dental MRI system 100 also includes a head rest arm 124. One end of the head rest arm 124 is attached to the supporting platform 106, for example. An opposite end of the head rest arm 124 is attached to or in contact with a head rest assembly 126, which includes the head holders 127a-127b. While the patient's forehead is held in contact with the head rest assembly 126, the patient's head is maintained in a fixed position by the head rest assembly 126. Information indicating a three-dimensional position of the head rest assembly 126 can be predetermined and stored, for example in a memory such as the secondary memory 234. Additionally, information indicating dimensions of the head rest assembly 126 can be predetermined and stored in that memory as well.

Figure 1C:
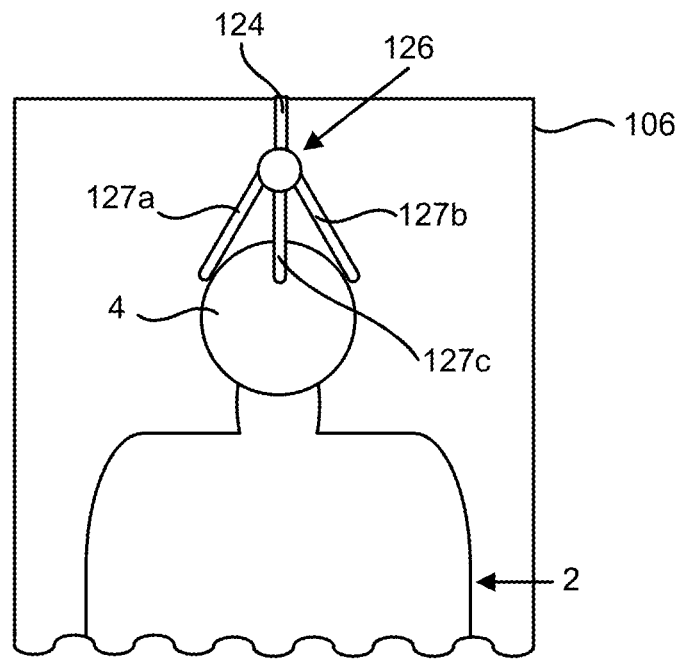
FIG. 1C illustrates a portion of a supporting platform and head rest assembly that can be used with the dental MRI system shown in FIG. 1A

In one embodiment, the length of the head rest arm 124 is known (i.e., predetermined). The head rest assembly 126 shown in FIG. 1C can include one or more step motors (not illustrated) that move one or more of the head holders 127a-127c until they touch (and stabilize) the head 4 of the patient 2. The step motors generate position information that is provided to the computer processor 222, which uses the position information to determine positions of each of the head holders 127a-127c. Because the head 4 of the patient 2 is positioned between the head holders 127a-127c, the position of the head 4 can be determined based on the positions of the head holders 127a-127c.

A primary function of the head holders 127a-127c of the head rest assembly 126 is to fix the head 4 of the patient 2 in a known or predetermined position. In one embodiment, the head rest assembly 126 includes a fixed-sized cushion.

In another embodiment, the head rest assembly 126 includes a variable-sized cushion that can be inflated or deflated with air, for example, to change the thickness of the cushion. For example, the head 4 of the patient 2 can be positioned on the cushion (or in between two or more cushions). The cushion(s) can be inflated or deflated until a predetermined pressure is obtained within the cushion(s) by virtue of the cushion(s) touching the head 4 of the patient 2. The pressure within the cushion(s) can be measured with a conventional pressure sensor (not illustrated), for example.

The dental MRI system 100 also includes a bite plate arm 120. One end of the bite plate arm 120 is attached to the supporting platform 106, for example (although not shown in FIG. 1A for convenience). An opposite end of the bite plate arm 120 is removably attached to a bite plate 122. While the patient 2 bites down on the bite plate 122, the patient's mouth is maintained in a fixed or predetermined location/position by the bite plate 122. Information indicating a three-dimensional location of the bite plate 122 can be predetermined and stored, for example, in a memory such as the secondary memory 234. Additionally, information indicating dimensions of the bite plate 122 can be predetermined and stored, for example, in the secondary memory 234. Because the dimensions of the bite plate arm 120 are known or predetermined, the position of the bite plate 124 also can be known or predetermined criteria.

The primary function of the bite plate 122 is to fix the teeth (not shown) of the patient 2 in a known or predetermined position. A secondary function of the bite plate 122 can be to position one or more HF coil 114, which in one example may be integrated into the bite plate 122. The location of the bite plate 122 defines a position or location of a patient's front teeth as well as a position or location of the patient's jaw. The secondary memory 234, for example, can store predetermined information indicating a position of the bite plate 122 with respect to a predetermined position or location of the dental MRI device 100. Any reference point can be used as the predetermined position or location of the dental MRI device 100, so long the same reference point is used consistently. For example, the origin of the coordinate system can be the geometrical center of the main magnet 216.

By way of example, the secondary memory 234 can store information indicating the length of the bite plate arm 124 and two angles (not shown) formed between the bite plate arm 124 and the first housing portion 102a, along with information indicating a position or location of a base portion of the bite plate arm 124 with respect to the predetermined position or location of the dental MRI system 100. The computer processor 222 can use this information to determine a position of the bite plate 126 with respect to a base of the bite plate arm 124.

The secondary memory 234, for example, also can store information indicating a position or location of each of a plurality of anatomical structures having a predetermined position or location with respect to a model patient's front teeth (or jaw). The camera unit 250 can be used to measure a distance between front teeth of the patient 2 and another anatomical landmark of the patient 2 (e.g., a cheek of the patient 2). The computer processor 222 can use the measured distance to estimate a position of a third anatomical structure (e.g., a particular tooth of interest). Additionally, the secondary memory 234 can store information representing a model of the patient 2, which the computer processor 222 uses to estimate a position of a particular anatomical structure (e.g., a particular tooth of interest).

After position information indicating the position of the bite plate 122 with respect to the predetermined location of the dental MRI device 100 is determined or retrieved from storage, the computer processor 222 can use this information along with the information indicating the positions of the anatomical structures to determine a location or position of any of those anatomical structures with respect to the predetermined location of the dental MRI device 100.

The secondary memory 234, for example, also can store predetermined information indicating a position or location of each of a plurality of anatomical structures having a predetermined position or location with respect to a patient's forehead. The camera unit 250 can be used to measure a size of an actual patient's forehead and a scaling factor can be determined and used to modify the information indicating the positions of the anatomical structures accordingly. For example, if the computer processor 222 determines, based on the image data captured by the camera unit 250, that the actual patient's forehead is 1.1 times smaller than the model patient's forehead, the computer processor can scale down the information indicating the positions of the anatomical structures by a factor of 1.1.

Alternatively, instead of simply scaling the information indicating the positions of the anatomical structures, dimensions of the patient's anatomical properties can be used as an input to a biometrical model that includes information about predefined anatomical structures. For example, information regarding a size of the patient's forehead, a distance between the patient's eyes, and/or dimensions of the patient's chin can be used as an input to a biometrical model that includes information regarding a distance between the patient's front teeth and/or one of the patient's molars. The computer processor 222 can process the input to the biometrical model in conjunction with the biometrical model to determine a most probable value for a position of a particular anatomical structure to be scanned.

After position information indicating the position of the head rest assembly 126 (and thus, the patient's forehead) with respect to the predetermined location of the dental MRI device 100 is determined or retrieved from storage, the computer processor 222 can use this information along with the information indicating the positions of the anatomical structures to determine a location or position of any of those anatomical structures with respect to the predetermined location of the dental MRI device 100.

All of the foregoing position and/or size determinations can be made using known algorithms.

Figure 3:
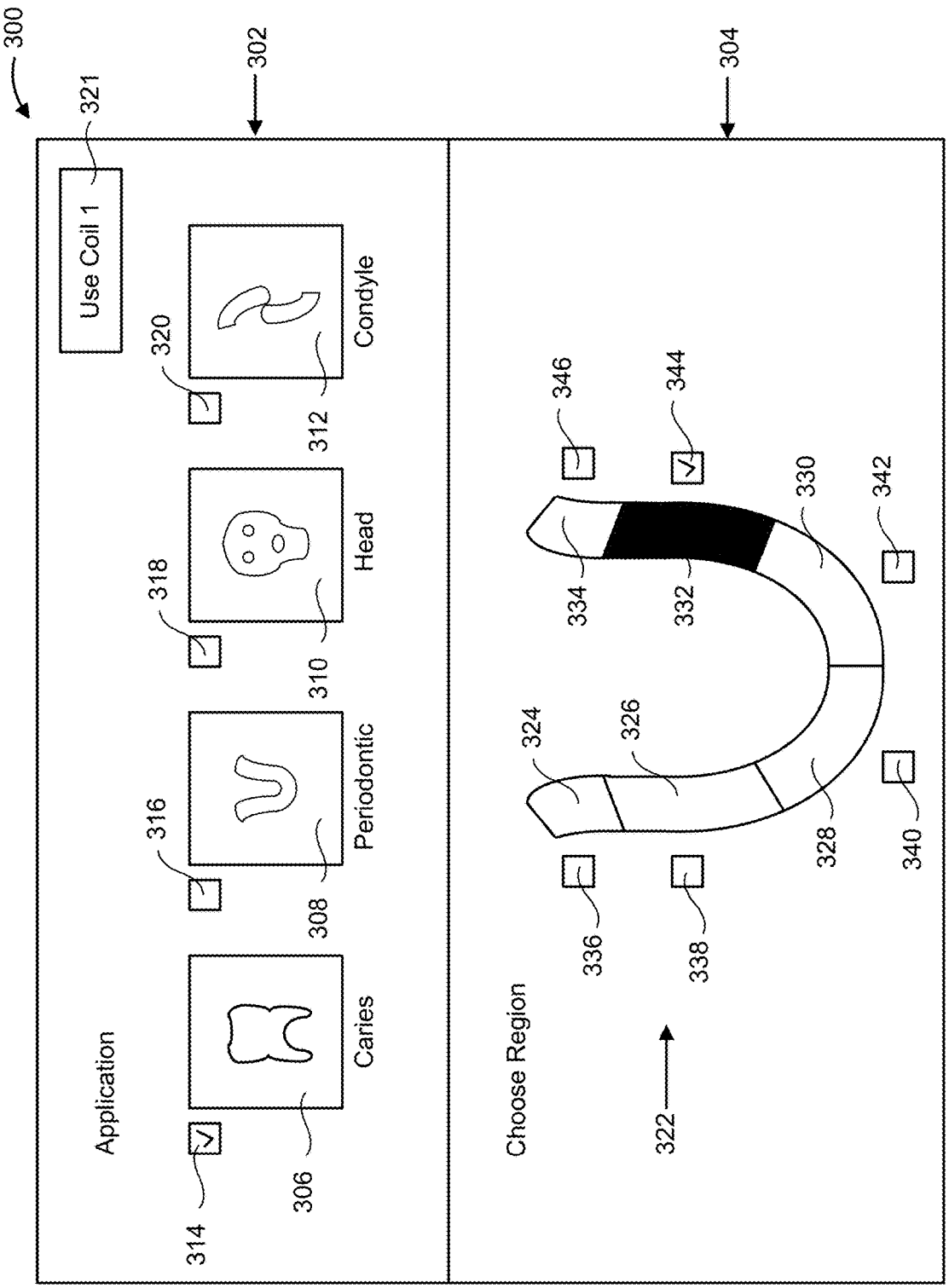
FIG. 3 illustrates a screen of a user interface displayed by a dental MRI system according to an example embodiment herein.

FIG. 3 illustrates a user interface screen 300 displayed by a dental MRI system according to an example embodiment herein. The screen 300 can be displayed, for example, using the display unit 228. The user interface screen 300 includes a first portion 302 and a second portion 304.

A plurality of indicators of a plurality of applications (e.g., dento-maxillofacial applications) that respectively correspond to different types of diagnostic inquiries is displayed in the first portion 302 of the screen 300. More particularly, the illustrated example includes an indicator 306 corresponding to a Caries Application, an indicator 308 corresponding to a Periodontal Application, an indicator 310 corresponding to a Head Application, and an indicator 312 corresponding to a Condyle Application displayed in the first portion 302 of the screen 300. The Caries Application is used to investigate one or more of the patient's teeth using a recording sequence that is appropriate for measuring hard substances (e.g., dentin and enamel) and generating a corresponding image with a high contrast. The Periodontal Application is used to investigate one or more portions of the patient's jaw using a recording sequence appropriate for measuring soft tissue and/or Periodontal inflammations and generating a corresponding image with a high contrast. The Head Application is used to investigate one or more portions of the patient's head using a recording sequence that is appropriate for measuring portions of the patient's head and generating a corresponding image with a well balanced contrast between different types of tissues. The Condyle Application is used to investigate one or more portions of the patient's mandibular condyle of the patient's temporomandibular joint using a recording sequence appropriate for measuring movements of the jaw and generating corresponding images with good temporal resolution.

Also displayed in the first portion 302 of the screen 300 are operator-selectable check boxes 314-320 corresponding to the indicators 306, 308, 310, and 312, respectively. Each check box can be selected to select a corresponding one of the applications and can be de-selected to de-select that application. Of course, such selection/de-selection of applications can be accomplished via an interface that includes one or more buttons, via a touch screen, or another type of user interface (e.g., a mouse of the input unit 230 shown in FIG. 2B). In response to one of the check boxes 314-32 being selected or de-selected, a processor (e.g., processor 222) receives an indication of the selected or de-selected application. The screen 300 can be displayed by the user interface unit 200 shown in FIG. 2A.

The first portion 302 of the screen 300 can also include an area 321 in which a particular HF coil 114 is identified. For example, in response to an operator selecting the check box 314 to select the Caries application, the processor 222 can cause the area 321 to display a message instructing the operator to use a particular HF coil 114 (e.g., a coil marked "1"). When the operator selects the check box 314, the processor 222 also can cause the indicator 115 of the particular HF coil 114 to become illuminated (or to change color, or to change a pattern or rate of blinking) to indicate to the operator that the particular HF coil 114 is to be used with the selected application.

Alternatively, the application can be selected automatically, without user interaction. For example, the secondary memory 234 can store patient history information (e.g., an amount of metal fillings) and the processor 222 can select one of a plurality of dento-maxillofacial applications based on the stored patient history information.

When one of the applications is selected, as described above, a graphical indicator 322 of an anatomical region or component corresponding to the selected application is displayed in the second portion 304 of the screen 300. The graphical representation can be based on a generic patient model or an image generated during a previous scan of an earlier investigation, such as an X-ray computed tomography (CT) scan, an ultrasound scan, a previous diagnostic image, a magnetic resonance image (MRI) scan, or a magnetic resonance tomography (MRT) scan. For example, when the operator uses the input unit 230 to select the check box 318, the processor 222 responds by causing a graphical indicator to be displayed in the second portion 304 of the screen 300. In this example, the graphical indicator is a graphical representation of a head region. The graphical indicator can be a representation of a stored schematic image or an actual image of a portion of the patient's body, for example, acquired with the digital camera unit 250. In response to a selection of one of the applications, the processor 222 can receive information representing characteristics of an object to be investigated, for example, a size of the patient's head and one or more indications of known anomalies from a storage device (e.g., secondary storage 234). This information can be generated from former scans with MRI or with other modalities such as CT and optical surface scan, for example.

For example, the computer processor 222 can use information generated during a previous CT or MRT scan of a jaw of a patient to determine the positions of individual teeth. By way of another example, the secondary storage 234 can store information representing a generic patient model and the computer processor 222 can obtain information representing the positions of individual teeth from the generic patient model stored in the secondary storage 234. By way of another example, the secondary storage 234 can store information representing a model of an object to be scanned (e.g., a model patient's teeth or jaw) and the computer processor 222 can determine a position of at least part of the patient (e.g., a particular tooth) with respect to the ROI using the model of the object to be scanned.

The graphical indicator of the head region can be divided into a plurality of regions. A plurality of check boxes also can be displayed adjacent the region, wherein each check boxes corresponds to a respective one of the regions. When the operator causes a check to appear in one of the check boxes, a corresponding one of the regions is selected. As a result, the processor 222 causes the selected region to be displayed in a special or otherwise highlighted state (e.g., in a particular color) to indicate that it has been selected. Similar functionality also is performed with respect to the other check boxes and regions shown in portion 304 of the screen 300.

In an example embodiment, if based on a prior examination, the patient 2 is known to have caries (e.g., cavities or tooth decay) in a particular location of the patient's mouth, the dental MRI system 100 can store data indicating the type of application (e.g., Caries Application) and the location of the caries. During a subsequent examination, an identifier of the patient can be input into the dental MRI system 100, which causes the Caries Application and the location of the caries to be selected automatically, without requiring an operator to select one of the applications and/or a particular region to be examined.

For example, sometimes caries at an early stage are not treated and are left to heal (i.e., remineralization). After a predetermined amount of time, another examination can be performed to monitor the extent to which the caries are healing.

In an example embodiment, the HF coil unit 210 includes a receptacle into which a portion of one of a plurality of different types of HF coils 114 can be inserted. The HF coil unit 210 can recognize the type HF coil 114 that is currently inserted into the receptacle. For example, each HF coil 114 can include a memory unit storing a unique coil identifier that is read by the receptacle. Each of the different types of HF coils 114 is used for a particular application. When the HF coil unit 210 recognizes a particular type of HF coil 114 (e.g., a type used to conduct investigations of caries), the HF coil unit 210 sends the computer processor 222 an indication of the recognized type of the HF coil 114, which the computer processor 222 uses to automatically select a particular application (e.g., the Caries Application), without requiring a user to manually select that application via the input unit 230.

Alternatively, the computer processor 222 can provide a set of possible applications for the particular HF coil 114 detected. For example, if two of the applications can be used with the recognized HF coil 114, but with other of the applications, the computer processor 222 can cause a dialog box to be displayed by which a user can select between the two applications that can be used with the recognized HF coil 114.

Figure 4:
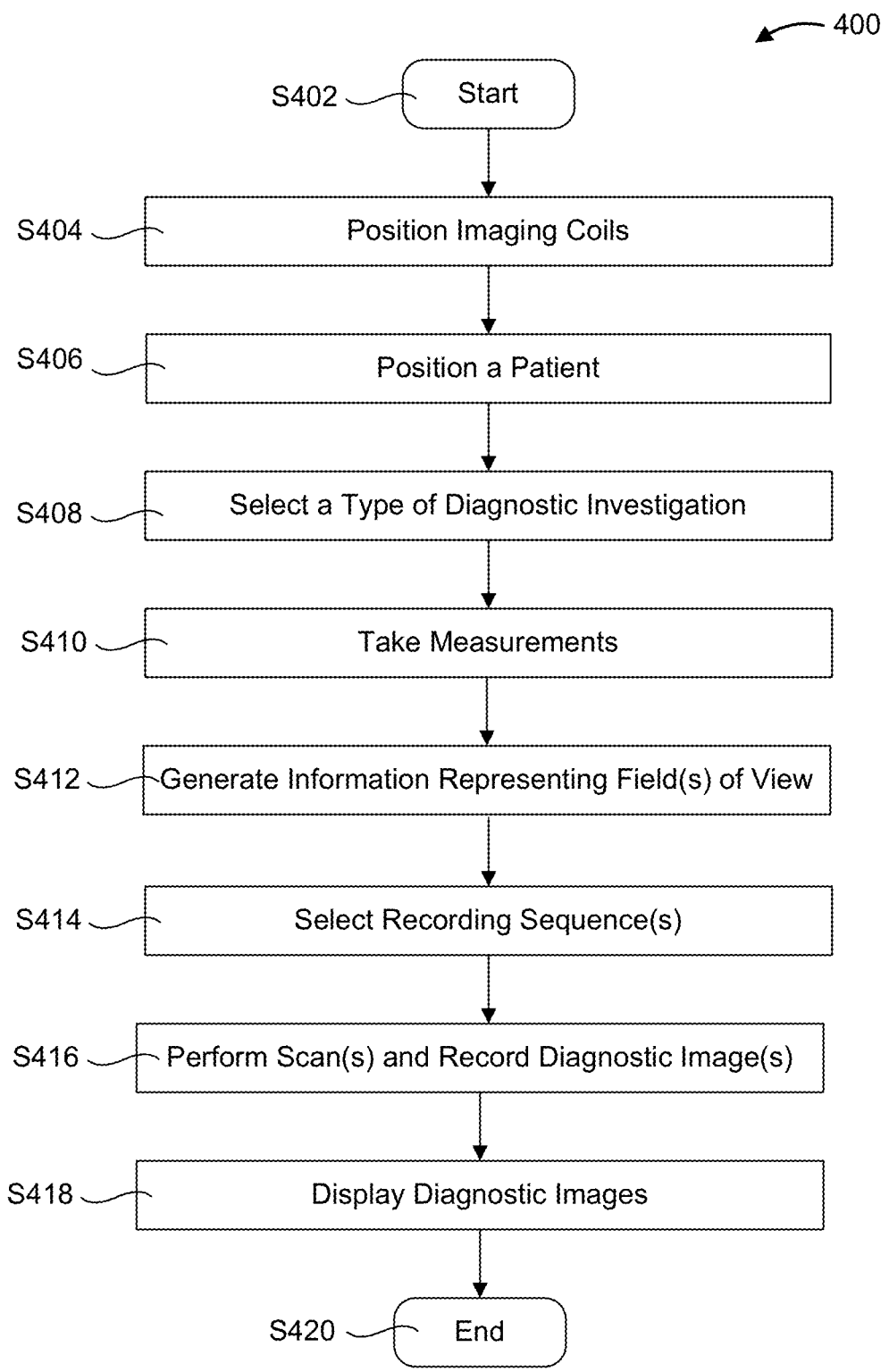
FIG. 4 is a flow diagram of a process for performing a diagnostic examination using an MRI system according to an example embodiment herein.

A procedure according to an example embodiment herein will now be described. FIG. 4 is a flow diagram 400 of a process that can be performed when an MRI system, such as the dental MRI system 100, is operated to conduct a diagnostic examination. The process begins in Step S402.

In Step S404, at least one imaging or HF coil (e.g., HF coil 114) is positioned near a portion of the patient's body that is to be examined (e.g., by moving the coil arm 112 to place the HF coil 114 near the patient's mouth), a position of the HF coil is determined, and information identifying the position of the HF coil is stored. If an MRI scan is to be performed using an imaging coil that is internal to the second housing portion 102*b*, for example, Step S404 can be omitted.

In Step S406, part of a patient's body (e.g., one or more teeth, a head, a jaw, a temporomandibular joint, etc.) is positioned in the MRI system. For example, using the dental MRI system 100 shown in FIG. 1A, the patient's head 4 can be positioned between head holders 127*a*-127*c*, the patient 2 can bite down on the bite plate 122, and/or place her head 4 against the head rest assembly 126.

While the patient 2 is positioned in this manner, the patient's teeth, for example, are located within a certain three-dimensional region or volume. The location of the bite plate 122 can be defined by the location of the ROI. The ROI can be within a FoV (of the system 100), for example, that is centered on the center of the main magnet 216. If the ROI is to include a molar tooth of a patient, for example, front teeth of the patient (and thus the bite plate 122) need to be positioned somewhere off-center from the center of the main magnet 216. The position of the bite plate 122 can be indicated by an intersection of lines formed by a laser in a known manner. Accordingly, the bite plate 122 itself need not be included in a target volume.

In addition, Step S406 can include taking an optical measurement of an object (e.g., one or more teeth) to be examined to precisely determine a three-dimensional region occupied by the object with respect to a predetermined location of the dental MRI system 100. For example, the digital camera unit 250 acquires one or more images of the patient's head and the processor 222 processes corresponding image data to determine a three-dimensional region occupied by the object relative to a predetermined location of the dental MRI system 100.

In an example embodiment, Step S406 can include fixing visual markers to predetermined locations on an object (e.g., the patient's head 4 or the bite plate 122) and using the digital camera unit 250 to acquire image data including markers. The digital camera unit 250 transfers the acquired image data to the computer processor 222 via the communications infrastructure 224. The computer processor 222 uses the image data and known algorithms to determine absolute positions of the markers. Because the relative positions of the markers with respect to the object are predetermined and thus known beforehand, the computer processor 222 can determine an absolute position of the object.

In an example embodiment, the patient is positioned in a fixed position that is outside of the main magnet 216. For example, the patient is initially positioned on the supporting platform 106. The position of the ROI with respect to the supporting platform 106 is known or predetermined. The supporting platform 106 supporting the patient is then positioned inside the main magnet 216. The position of the supporting platform 106 with respect to the main magnet 216 can be either predetermined or measured, such that the position of the ROI with respect to the main magnet 216 also is known or predetermined.

In Step S408, the operator selects one or more applications to be executed corresponding to the type(s) of diagnostic investigation to be performed, by selecting one or more corresponding check boxes 314, 316, 318, 320. In Step S408, the operator also can select one or more regions of interest in the second portion 304 of the screen 300, which are displayed in the portion 304 in response to the selection(s) made in first portion 302 of the screen 300, for example.

In Step S410, measurements are taken to generate information indicating a three-dimensional region where the imaging or HF coil (e.g., HF coil 114) is located, with respect to a predetermined location of the dental MRI system. For example, the measuring device 116 measures the angles $\alpha$ and $\beta$, as described above, and the processor 222 causes information indicating values of the angles $\alpha$ and $\beta$ to be stored in main memory 232. The processor 222 uses this information along with the stored information indicating the dimensions of the coil arm 112 and the HF coil 114 to generate information indicating the three-dimensional region occupied by the HF coil 114 with respect to a predetermined location of the dental MRI system 100. The processor 222 causes the generated information indicating the three-dimensional region occupied by the HF coil 114 to be stored, for example, in main memory 232.

In an example embodiment (not shown), the imaging coil is fixed to the dental MRI system and is not movable. In this embodiment, it is not necessary to take measurements of the location of the imaging coil. Instead, predetermined information indicating the three-dimensional region where the imaging coil is located can be stored, for example, in the secondary memory 234.

Step S410 also can include taking an optical measurement of a position of the imaging coil (e.g., HF coil 114). For example, the digital camera unit 250 can be mounted at a predetermined location on the dental MRI system 100 and can acquire an image of the HF coil 114. The processor 222 can process corresponding image data and determine a location or three-dimensional region occupied by the HF coil 114 relative to the predetermined location of the dental MRI system 100. The processor 222 causes the generated information indicating the three-dimensional region occupied by the HF coil 114 to be stored, for example, in the main memory 232.

To determine the three-dimensional position of the HF coil 114, a plurality of optical markers can be attached to the HF coil 114. The camera unit 250 can generate data representing a two-dimensional image of the HF coil 114. The computer processor 222 can process the data representing the two-dimensional image of the HF coil 114 and determine one or more distances between the optical markers. The computer processor 222 can use the determined distance to calculate the three-dimensional position of the HF coil 114 using known techniques.

Alternatively, the camera unit 250 can be a stereoscopic camera system that includes two cameras, each of which generates data representing a two-dimensional image of the HF coil 114. The computer processor 222 can determine the three-dimensional position of the HF coil 114 by processing the data representing the two-dimensional images of the HF coil 114 using known triangulation techniques.

Moreover, in Step S410 measurements also can be taken to generate information indicating a target volume or three-dimensional region where a target object (e.g., one or more teeth) is to be imaged. For example, the digital camera unit 250 can acquire one or more images of the object and the processor 222 can process corresponding image data to determine a location or three-dimensional region occupied by the object relative to a predetermined location of the dental MRI system 100. The processor 222 causes the generated information indicating the target volume or three-dimensional region occupied by the object to be stored, for example, in the main memory 232.

Alternatively, Step S410 can include generating information indicating a target volume or three-dimensional region of an object, without taking measurements of the object. For example, when the Caries Application has been selected as the type of diagnostic inquiry in Step S408, the processor 222 uses the stored information indicating the three-dimensional region occupied by the bite plate 122 relative to a predetermined location of the dental MRI system 100 and stored information indicating expected sizes of one or more anatomical structures, for example, the expected size of a mandibular bone of a patient, to determine a three-dimensional region occupied by the patient's teeth with respect to a predetermined location of the dental MRI system 100.

In Step S412, information representing one or more field(s) of view for imaging is generated. In one example, information representing the FoV for imaging can be generated automatically (without being in response to a user command) based on a predetermined position or a measured position of the ROI and the ROI's expected size for a particular application. In other examples, the information can be generated in response to a user command.

The size of the ROI can be a predetermined size for use with the type of diagnostic investigation selected in Step S408. For example, if the Carries Application is selected in Step 408, the size of the ROI can be predetermined to encompass an average-sized tooth; if the Head Application is selected in Step 408, the size of the ROI can be a predetermined size to encompass an average-sized head. Values representing predetermined sizes of various regions of interest that are expected to be used for each type of diagnostic application can be stored in the secondary memory 324. The computer processor 222 can retrieve a particular value representing a predetermined size of a ROI in Step S412.

A measurement of a part of a patient (e.g., one or more teeth or a head) can be performed and the information representing the expected size of the ROI can be scaled based on a measured size of the part of the patient. For example, if the patient's head is measured to be ten percent larger than an average-sized head, the computer processor 222 can scale-up the size of the ROI retrieved from the secondary memory 324 by ten percent and use the scaled-up size of the ROI to generate the information representing the field of view.

Information representing the position of the ROI can be predetermined information that is based on the type of diagnostic investigation selected in Step S408. For example, if the check box 314 and the check box 344 of the user interface screen 300 are selected in Step S408, the computer processor 222 can obtain previously generated ROI information stored in the secondary memory 234 in Step S412, wherein the position of the ROI is such that the ROI includes a particular tooth of an average patient that is included in the region 332 shown in FIG. 3.

Additionally, a measurement of a part of a patient can be performed and information representing a position of the ROI can be scaled based on a measured size of the part of the patient. For example, the camera unit 250 can be used to measure a distance between front teeth of the patient 2 and a predetermined part of a cheek of the patient 2. The computer processor 222 can use the measured distance to estimate a position of a particular tooth to be investigated (e.g., a molar). The position of an ROI that is based on the type of diagnostic investigation selected in Step S408 can be adjusted so that the ROI encompasses the particular tooth to be investigated.

Alternatively, Step S412 can include generating information representing the position of the ROI using information generated in Step S410. For example, once the three-dimensional position of the HF coil 114 has been determined as described above in connection with Step S410, information representing a predetermined three-dimensional offset from the HF coil 114 can be added to the determined position of the HF coil 114 to generate the information representing the position of the ROI.

In Step S414, one or more recording sequences are selected based on the information representing the one or more fields of view generated in Step S412. In one example, a recording sequence is a predefined set of at least one HF pulse value and at least one gradient pulse value, which can be repeated many times during a diagnostic scan, time interval values between pulses, amplitude values of waveforms, shape values of waveforms, and length values of waveforms. The recording sequence can be generated by a highly-skilled technician using a MRI system, for example, and stored in the secondary memory 234.

A recording sequence also can include, in one example, timing values for measuring and reading out received HF signals. For example, a particular recording sequence is generated based on (1) a position or location of a patient's body part (e.g., a tooth or other body part) to be imaged, (2) a field of view that can be determined by a position or location and characteristics of the imaging coil, (3) the type of application selected, (4) characteristics of the patient's body part to be imaged (e.g., the body part is soft tissue, the body part is bone, and a size of the body part) and characteristics of other body parts surrounding the body part to be imaged, and (5) a resolution of an image required for a particular diagnostic evaluation. The recording sequence can be selected automatically, without user interaction, when items (1)-(5) above are known or determined.

For example, a highly-skilled technician can generate recording sequences for a variety of different types of dental applications and for a variety of different regions of a patient's body, and store these recording sequences in the secondary memory 234. Subsequently, a less-skilled technician can operate the user interface 200 and select the Caries Application as the type of diagnostic inquiry to be performed and select Region 332 as the region to be scanned. After the HF coil 114 has been positioned near the patient and measurements are taken in Step S410, the computer processor 222 determines the position of the HF coil 114 (and/or the position/size of the patient's head, the position of the bite plate 122, and the position of the head rest assembly 126). The computer processor 222 then selects one or more recording sequence(s) to be used from among the predetermined recording sequences stored in the secondary memory 234. At least one of the following types of information is used to select the recording sequence(s): the selected type of diagnostic inquiry, the region to be scanned, the position of the HF coil 114, the position/size of the patient's head, the position of the bite plate 122, the position of the head rest assembly 126, and information indicating the FoV (see Steps 404-S412 above). In some examples, one or more of those types of information can be predetermined (pre-stored prior to performance of the method herein) and/or one or more of the types of information can be determined as described above in the context of Steps S410 and S412, where applicable.

In Step S416, the dental MRI system 100 uses the recording sequence(s) selected in Step S414 to perform one or more MRI scans of the object (e.g., a tooth) and to acquire data for forming one or more diagnostic images in a known manner. More particularly, excitation and measurement signals are transmitted and received by the HF and gradient coils based on parameters (e.g., parameters such as those described above) included in each recording sequence for each MRI scan. When multiple recording sequences are used, multiple diagnostic inquiries can be performed consecutively, which makes it possible to obtain different properties of the object, at multiple resolutions, and with multiple degrees of contrast.

The recording sequence(s) are used to acquire diagnostic data. After the diagnostic data has been acquired, the computer processor 222 processes the diagnostic data to construct a diagnostic image. Data representing the diagnostic image can be stored in the secondary memory 234 and/or displayed by the display unit 228, for example.

For example, in response to check box 344 being selected in Step S408, the processor 222 automatically generates a recording sequence based on the selected type of investigation, the selected region, the position of the object to be examined, and the position of the imaging coil. Because the dental MRI system 100 automatically selects the recording sequence(s), the operator is not required to possess knowledge concerning a correlation between a particular recording sequence and a particular diagnostic inquiry. Additionally, a technician operating the MRI system 100 need not enter parameters associated with the recording sequence(s) via the user interface unit 200, for example, which can be a time-consuming process and can require a highly skilled technician.

Figure 6:
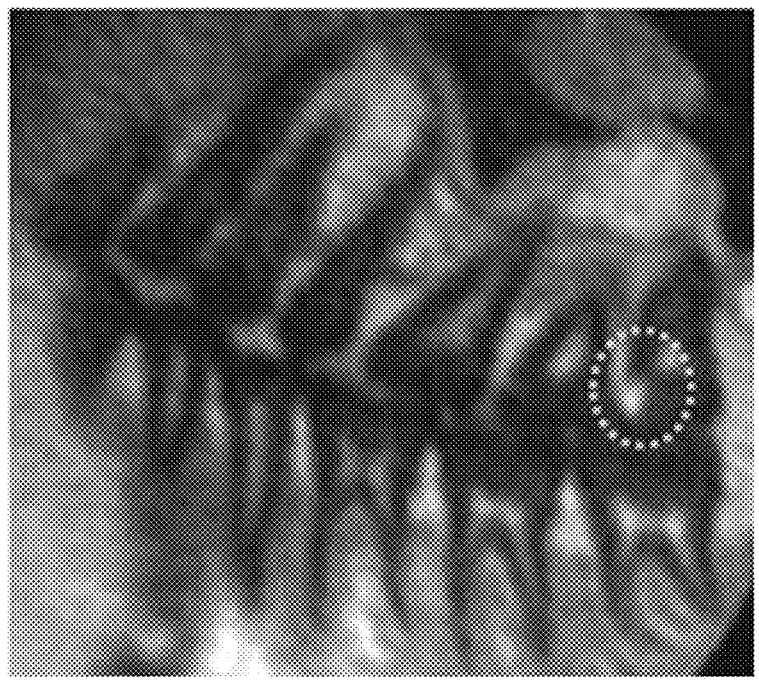
FIG. 6 is an example of a diagnostic image that can be generated by the dental MRI system shown in FIG. 1A.

In Step S418, one or more of the images recorded in Step S416 are displayed. For example, the display unit 228 displays the image(s) recorded in Step S414, such as the image 600 shown in FIG. 6. The displayed images can correspond to multiple diagnostic inquiries. The display of the images can be optimized based on the selected type(s) of diagnostic investigations. For example, information relevant for the selected application is enhanced in the displayed image and information that is not relevant is reduced, which can assist a medical professional to quickly make an accurate diagnosis. Additionally, for the Caries Application, a contrast ratio of the display unit 228 is optimized such that caries are enhanced in the displayed image. The process ends in Step S420.

Figure 5:
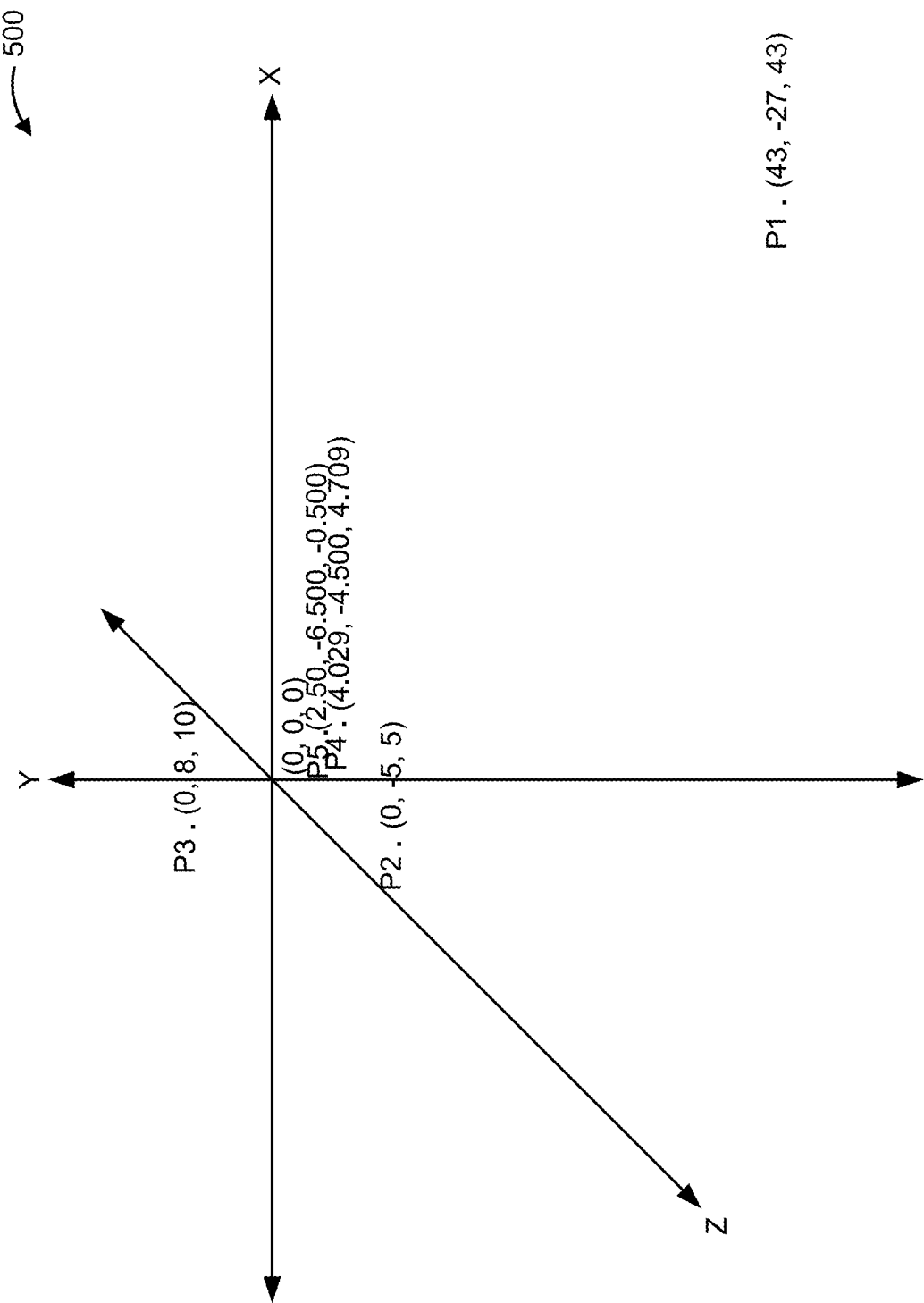
FIG. 5 shows a coordinate system of a dental MRI system according to an example embodiment herein.

FIG. 5 shows an example rectangular coordinate system 500 that can be used by the dental MRI system 100. The origin of the coordinate system can be any point of the dental MRI system 100. In one example embodiment, the main magnet 216 has a toroidal or doughnut shape, and the origin corresponds to a geometric center of the main magnet 216. In this example, a point P1 corresponds to a location at the base of the measuring device 116, a point P2 corresponds to a location at front and center of the bite plate 122, and a point P3 corresponds to a location at the front and center of the head rest assembly 126.

In this example, the point P1 has coordinates of (43, −27, 43) in units centimeters. Of course, any other desired unit of measure can be used. Also, in this example, assume that the coil arm 112 has a length of 45 centimeters and, for illustrative simplicity in this example, that a center of the HF coil 114 is located at the end of the coil arm 112 where the HF coil 114 is attached to the coil arm 112. Additionally, in this example, after the coil arm 112 is moved in to an appropriate position near a patient, the measuring device 116 generates data indicating that the values of the angles $\alpha$ and $\beta$ are 60° and 45°, respectively. Finally, for illustrative simplicity in this example, assume that the end of the coil arm 112 that is connected to and pivots from the second housing portion 102*b* at the point P1.

To determine an absolute position of the center of the HF coil 114, the computer processor 222 can first determine a relative position of the HF coil 114 with respect to the point P1, which corresponds to a predetermined location at the base of the measuring device 116, and then translate the relative position of the HF coil 114 to an absolute position of the center of the HF coil 114 with respect to the origin of the coordinate system 500. The relative position of the HF coil 114 with respect to the point P1 can be determined by calculating X, Y, and Z coordinates of the center of the HF coil 114 with respect to the point P1. This can be accomplished using the values of the length of the coil arm 112 and the values of the angles $\alpha$ and $\beta$.

More particularly, the magnitude of the X coordinate is sine $\alpha$ times the length of the coil arm 112 (X=sin 60°×45 cm=38.971 cm), and because the HF coil 114 extends from the point P1 in the negative X direction, the result is multiplied by −1. The Y coordinate is cosine $\alpha$ times the length of the coil arm 112 (Y=cos 60°×45 cm=22.5 cm). The Z coordinate is cosine $\beta$ times the length of the coil arm 112 (Z=cos 45°×45 cm=38.291 cm), and because the HF coil 114 extends from the point P1 in the negative Z direction, the result is multiplied by −1. Accordingly, the relative position of the center of the HF coil 114 is determined to be (−38.971, 22.500, −38.291) with respect to the point P1.

Next, the coordinate for the position of the center of the HF coil 114 with respect to the point P1 is translated to an absolute coordinate of the center of the HF coil 114 with respect to the origin of the coordinate system 500. This can be accomplished by adding the absolute coordinate of the point P1 to the coordinate of the position of the center of the HF coil 114 with respect to the point P1. Accordingly, the absolute position of the center of the HF coil 114 is determined to be (4.029, −4.500, 4.709), which is shown as point P4 in FIG. 5.

Additionally, in this example, the secondary memory 234 stores information representing coordinates of a plurality of different teeth with respect to the point P2. Further, in this example, assume that the processor receives a coordinate of (2.500, −1.500, −4.500) relative to the front, center point of the bite plate 122 (the point P2) for a tooth included in the region 332 shown in FIG. 3, in response to a check being placed in the check box 344. The absolute coordinate of the tooth can be determined by adding the relative coordinate for the tooth to the absolute coordinate for the point P2. Accordingly, the coordinate of the tooth relative to the origin of the coordinate system 500 can be determined to be (2.50, −6.500, −0.500), which is shown an point P5 in FIG. 5.

Alternatively, in this example, the secondary memory 234 stores information representing coordinates of a plurality of different teeth with respect to the point P3. Further, in this example, assume that the processor receives a coordinate of (2.500, −14.500, −9.500) relative to the front, center point of the head rest assembly 126 (the point P3) for a tooth included in the region 332 shown in FIG. 3, in response to the check box 344 being selected. The absolute coordinate of the tooth can be determined by adding the relative coordinate for the tooth to the absolute coordinate for the point P3. Accordingly, the coordinate of the tooth relative to the origin of the coordinate system 500 can be determined to be (2.50, −6.500, −0.500), which is shown the point P5 in FIG. 5.

The values used in the foregoing examples described in conjunction with FIG. 5 are for illustrative purposes only. The dental MRI system 100 is not limited to these values.

As will be appreciated by those of skill in the relevant art(s) in view of this description, the example aspects described herein can be implemented using a single computer or using a computer system that includes multiple computers each programmed with control logic to perform various of the above-described functions.

The various embodiments described above have been presented by way of example and not limitation. It will be apparent to persons skilled in the relevant art(s) that various changes in form and detail can be made therein (e.g., different hardware, communications protocols, and the like) without departing from the spirit and scope of the present invention. Thus, the present invention should not be limited by any of the above-described exemplary embodiments, but should be defined only in accordance with the following claims and their equivalents.

The foregoing description has been described in the context of example embodiments in which MRI systems include transmitting and receiving units. However, the present disclosure and invention are not limited to that structure only. Indeed, it also is within the scope of the invention to provide a dental MRI apparatus that works in conjunction with a conventional MRI apparatus that includes transmitting and receiving units. One skilled in the art will appreciate, in view of the present disclosure, how to adapt the system architecture and various steps of the method(s) described above, if at all, to interface a computer system, imaging coil assembly, and/or a digital camera unit to a conventional MRI apparatus to achieve similar functionality.

In addition, it should be understood that the attached drawings, which highlight functionality described herein, are presented as illustrative examples. The architecture of the present invention is sufficiently flexible and configurable, such that it can be utilized (and navigated) in ways other than that shown in the drawings.

Moreover, the example embodiments described herein are not limited to dental MRI systems. The example embodiments described herein can be used to perform diagnostic examinations of other anatomical regions. Moreover, although described herein in the context of an operator performing certain functions of the procedures herein, it should be understood that in other example, the procedures can be performed completely automatically, without operator input.

Further, the purpose of the appended Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way.

What is claimed is:

1. A method for operating a dental magnetic resonance imaging system that includes an imaging coil attached to a coil arm, the method comprising:
positioning the imaging coil near an object to be imaged;
receiving a selection of a dento-maxillofacial application from a plurality of dento-maxillofacial applications, the selected dento-maxillofacial application corresponding to a diagnostic inquiry;
causing a display device to display, in response to the selection of the dento-maxillofacial application, a graphical indicator of an anatomical region corresponding to the selected dento-maxillofacial application, wherein the graphical indicator of the anatomical region comprises one or more regions;
receiving a selection of a region of the one or more regions of the graphical indicator displayed on the display device;
selecting a magnetic resonance imaging recording sequence, from a plurality of magnetic resonance imaging recording sequences, based on: the selected dento-maxillofacial application, the selected region of the one or more regions of the graphical indicator, and a position of the imaging coil within the dental magnetic resonance imaging system, wherein the selected magnetic resonance imaging recording sequence includes one or more values that configure the dental magnetic resonance imaging system to perform a scan of the object to be imaged that corresponds to the diagnostic inquiry; and
scanning the object to be imaged using the dental magnetic resonance imaging system configured in accordance with the magnetic resonance recording sequence.

2. The method of claim 1, wherein the selecting of the magnetic resonance imaging recording sequence, from the plurality of recording sequences, is further based on field-of-view information.

3. The method of claim 2, wherein the field-of-view information is generated based on a position of a region of interest with respect to the object to be imaged and an expected size of the region of interest, and
wherein the object to be imaged is at least partially within the region of interest.

4. The method of claim 3, further comprising:
receiving a measured size of a part of a patient,
wherein the expected size of the region of interest is determined by scaling a predetermined size of the region of interest for the selected dento-maxillofacial application based on the measured size of the part of the patient.

5. The method of claim 3, wherein the position of the region of interest is determined by adjusting an initial position of the region of interest for the selected dento-maxillofacial application based on a measured size of a part of the patient.

6. The method of claim 3, wherein the position of the region of interest is determined by adding a predetermined three-dimensional offset to the position of the imaging coil.

7. The method of claim 1, further comprising:
causing a display device to display the plurality of dento-maxillofacial applications.

8. The method of claim 1, wherein the one or more values in the magnetic resonance imaging recording sequence include one or more of: a high frequency pulse value, a gradient pulse value, a time interval between pulses, a waveform amplitude, a waveform shape, a waveform length, and a timing value for measuring and/or reading out high frequency signals.

9. The method of claim 1, wherein the plurality of magnetic resonance imaging recording sequences are received from a non-transitory memory, and
wherein the plurality of magnetic resonance imaging recording sequences correspond to respective combinations of the plurality of dento-maxillofacial applications and regions of a patient's body.

10. The method of claim 1, further comprising:
generating a diagnostic image based on scan data from the scanning of the object to be imaged.

11. The imaging method of claim 1, wherein the selected dento-maxillofacial application is one of a caries application, a periodontal application, a head application, or a condyle application.

12. A dental magnetic resonance imaging system, the system comprising:
a magnetic resonance scanner constructed to perform a scan of an object, the magnetic resonance scanner including an imaging coil attached to a coil arm;
a display device; and
a processor connected to the magnetic resonance scanner and configured to:
receive a selection of a dento-maxillofacial application from a plurality of dento-maxillofacial applications, the selected dento-maxillofacial application corresponding to a diagnostic inquiry,
cause the display device to display, in response to the selection of the dento-maxillofacial application, a graphical indicator of an anatomical region corresponding to the selected dento-maxillofacial application, wherein the graphical indicator of the anatomical region comprises one or more regions,
receiving a selection of a region of the one or more regions of the graphical indicator displayed on the display device,
select a magnetic resonance imaging recording sequence, from a plurality of magnetic resonance imaging recording sequences, based on: the selected dento-maxillofacial application, the selected region of the one or more regions of the graphical indicator, and a position of the imaging coil within the dental magnetic resonance imaging system, wherein the selected magnetic resonance imaging recording sequence includes one or more values that configure the magnetic resonance scanner to perform scan of the object that corresponds to the diagnostic inquiry, and
generate a diagnostic image based on scan data produced during the scan of the object by the magnetic resonance scanner configured in accordance with the recording sequence.

13. The imaging system of claim 12, wherein the processor is further configured to select the magnetic resonance imaging recording sequence from the plurality of magnetic resonance imaging recording sequences based on field-of-view information.

14. The imaging system of claim 13, wherein the field-of-view information is generated based on a position of a region of interest with respect to the object and an expected size of the region of interest, and
wherein the object is at least partially within the region of interest.

15. The imaging system of claim 14, wherein the processor is further configured to receive a measured size of a part of a patient,
wherein the expected size of the region of interest is determined by scaling a predetermined size of the region of interest for the selected dento-maxillofacial application based on the measured size of the part of the patient.

16. The imaging system of claim 14, wherein the position of the region of interest is determined by adjusting an initial position of the region of interest for the selected dento-maxillofacial application based on a measured size of a part of the patient.

17. The imaging system of claim 14, wherein the position of the region of interest is determined by adding a predetermined three-dimensional offset to the position of the imaging coil.

18. The imaging system of claim 12, further comprising:
a user interface connected to the processor and configured to receive a user input and generate the selection of the dento-maxillofacial application in response to the user input.

19. The imaging system of claim 18, wherein the processor is further configured to cause the display device to display the plurality of dento-maxillofacial applications.

20. The imaging system of claim 12, wherein the one or more values in the magnetic resonance imaging recording sequence include one or more of: a high frequency pulse value, a gradient pulse value, a time interval between pulses, a waveform amplitude, a waveform shape, a waveform length, and a timing value for measuring and/or reading out high frequency signals.

21. The imaging system of claim 12, further comprising:
a non-transitory memory storing the plurality of magnetic resonance imaging recording sequences,
wherein the plurality of magnetic resonance imaging recording sequences correspond to respective combinations of the plurality of dento-maxillofacial applications and regions of a patient's body.

22. The imaging system of claim 12, wherein the processor is further configured to cause the display device to display the diagnostic image.

23. The imaging system of claim 12, further comprising:
a patient fixture constructed to position a part of a patient at a predetermined location.

24. The imaging system of claim 23, wherein the patient fixture includes a head rest assembly that is adapted to contact at least three points of a head of the patient.

25. The imaging system of claim 23, wherein the patient fixture includes a bite plate.

26. The imaging system of claim 23, wherein the patient fixture includes a cushion.

27. The imaging system of claim 23, wherein the processor is further configured to determine a position of a region of interest based on the predetermined location at which the part of the patient is positioned by the patient fixture.

28. The imaging system of claim 27, wherein a position of the imaging coil with respect to a position of the patient fixture is predetermined.

29. The imaging system of claim 23, wherein the patient fixture includes a bite plate, and
wherein the processor is further configured to determine a position of a region of interest using a position of the bite plate.

30. The imaging system of claim 23,
wherein the patient fixture includes a laser unit that produces crossing lines, and
wherein the processor is further configured to determine a position of a region of interest using a position of an intersection of the crossing lines.

31. The imaging system of claim 23, wherein the patient fixture includes a head rest assembly at a predetermined position, and
   wherein the processor is further configured to determine a position of a region of interest using the predetermined position of the head rest assembly.

32. The imaging system of claim 23, wherein the patient fixture includes a bite plate and the processor is further configured to determine a position of the part of the patient based on a position of the bite plate.

33. The imaging system of claim 23, wherein the patient fixture includes a laser unit, and the processor is further configured to determine a position of the part of the patient based on a position of an intersection of crossing lines produced by the laser unit.

34. The imaging system of claim 23, wherein the patient fixture includes a head rest assembly, and the processor is further configured to determine the position of the part of the patient based on a position of the head rest assembly.

35. The imaging system of claim 23, further comprising:
   at least one camera configured to measure a position of at least a part of the patient fixture.

36. The imaging system of claim 12, further comprising:
   a non-transitory memory constructed to store the plurality of dento-maxillofacial applications.

37. The imaging system of claim 36, wherein the non-transitory memory is further constructed to store patient history information, and
   wherein the processor is further configured to select the dento-maxillofacial application from among the plurality of dento-maxillofacial applications based on the patient history information.

38. The imaging system of claim 12, wherein the display device is a user interface configured to receive a user input and generate the selection of the dento-maxillofacial application in response to the user input.

39. The imaging system of claim 38, wherein the display device includes a touch screen or a button for receiving the user input.

40. The imaging system of claim 12,
   wherein the processor is further configured to (i) generate image data from data produced during a scan of the object by the magnetic resonance scanner configured in accordance with the magnetic resonance imaging recording sequence, and (ii) cause the display device to display an image corresponding to the image data.

41. The imaging system of claim 40, wherein the image is a two-dimensional slice of at least part of the object, the two-dimensional slice having a predefined orientation with respect to an anatomical structure.

42. The imaging system of claim 40, wherein the image is a dental panoramic view of the object.

43. The imaging system of claim 40, wherein the object is a patient, and
   wherein the image is a two-dimensional slice perpendicular to a maxillary crest of the patient.

44. The imaging system of claim 40, wherein the object is a patient, and
   wherein the image is a two-dimensional slice tangential to a maxillary crest of the patient.

45. The imaging system of claim 40, wherein the object is a patient, and
   wherein the image is a two-dimensional slice in a plane based on one or more dental roots of the patient.

46. The imaging system of claim 40, wherein the object is a patient, and
   wherein the image is a two-dimensional slice in a plane based on a transmandibular joint of the patient.

47. The imaging system of claim 40, wherein the processor is further configured to invert image colors in the image data and cause the display device to display the image with inverted colors.

48. The imaging system of claim 40, wherein the processor is further configured to:
   generate a suggestion for a diagnosis based on the selected dento-maxillofacial application and cause the display device to display the suggestion for the diagnosis.

49. The imaging system of claim 12, wherein the at least one imaging coil is positionable automatically.

50. The imaging system of claim 12, wherein the processor is further configured to select the magnetic resonance imaging recording sequence from the plurality of magnetic resonance imaging recording sequences based on patient-specific information.

51. The imaging system of claim 12, wherein the processor is further configured to determine a position of a part of the object with respect to a region of interest based on a model of the object.

52. The imaging system of claim 12, wherein the processor is further configured to determine a position of a part of the object with respect to a region of interest using information about the object from a previous scan.

53. The imaging system of claim 12, further comprising:
   a camera configured to generate image data of a part of a patient,
   wherein a measurement of a position of the part of the patient is based on the image data, and
   wherein the processor is further configured to determine a position of a region of interest based on the measurement of the position of the part of the patient.

54. The imaging system of claim 53, wherein the image data corresponds to an optical image.

55. The imaging system of claim 53, wherein the processor is further configured to determine the position of the part of the patient by automatically detecting the part of the patient in a scout image.

56. The imaging system of claim 53, wherein the position of the region of interest and the position of the part of the patient are identical.

57. The imaging system of claim 12, further comprising:
   at least one camera,
   wherein the at least one camera is configured to generate image data of the imaging coil,
   wherein the processor is further configured to determine the position of the imaging coil based on the image data.

58. The imaging system of claim 12, wherein the processor is further configured to determine a position of a region of interest using information generated by a previous MRI scan, a previous computed tomography scan, a previous ultrasound scan, or a previous optical image.

59. The imaging system of claim 12, wherein the magnetic resonance imaging recording sequence is of a spin-echo-sequence type.

60. The imaging system of claim 12, wherein the magnetic resonance imaging recording sequence is of a gradient-echo-sequence type.

61. The imaging system of claim 12, wherein the magnetic resonance imaging recording sequence is of an ultra-short-echo-time type.

62. The imaging system of claim 12, wherein the magnetic resonance imaging recording sequence is of a zero-echo-time type.

63. The imaging system of claim 12, wherein the magnetic resonance imaging recording sequence is of a SWIFT type.

64. The imaging system of claim 12, wherein the dento-maxillofacial application is selected based on the imaging coil connected to the imaging system.

65. The imaging system of claim 12, wherein the processor is further configured to cause the display device to identify the imaging coil based on the selection of the dento-maxillofacial application.

66. A non-transitory computer-readable storage medium storing computer-executable code that, when executed by a computer, causes the computer to perform a method comprising:

receiving a selection of a dento-maxillofacial application from a plurality of dento-maxillofacial applications, the selected dento-maxillofacial application corresponding to a diagnostic inquiry;

causing a display device to display, in response to the selection of the dento-maxillofacial application, a graphical indicator of an anatomical region corresponding to the selected dento-maxillofacial application, wherein the graphical indicator of the anatomical region comprises one or more regions;

receiving a selection of a region of the one or more regions of the graphical indicator displayed on the display device;

selecting a magnetic resonance imaging recording sequence, from a plurality of magnetic resonance imaging recording sequences, based on: the selected dento-maxillofacial application, the selected region of the one or more regions of the graphical indicator, and a position of an imaging coil attached to a coil arm of within a dental magnetic resonance imaging system, wherein the selected magnetic resonance imaging recording sequence includes one or more values that configure the dental magnetic resonance imaging system to perform a scan of an object to be imaged that corresponds to the diagnostic inquiry; and scanning the object to be imaged using the dental magnetic resonance imaging system configured in accordance with the magnetic resonance recording sequence.

\* \* \* \* \*